(12) United States Patent
Simon et al.

(10) Patent No.: US 8,476,058 B2
(45) Date of Patent: Jul. 2, 2013

(54) PROBIOTIC YEAST COMPOSITIONS AND METHODS FOR INFLAMMATORY DISEASES

(75) Inventors: Jean-Luc Simon, Lille (FR); Georges Pignede, Marcq en Baroeul (FR); Pascal Vandekerckove, Villeneuve d'Ascq (FR); Pierre Desreumaux, Marcq en Baroeul (FR); Daniel Poulain, Templeuve (FR); Arlette Darfeuille-Michaud, La Roche Blanche (FR); Adeline Sivignon, Clermont-Ferrand (FR)

(73) Assignees: Lesaffre et Compagnie (FR); Universite du Droit et de la Sante Lille 2 (FR); Universite d'Auvergne Clermont 1 (FR)

( * ) Notice: Subject to any disclaimer, the term of this patent is extended or adjusted under 35 U.S.C. 154(b) by 318 days.

(21) Appl. No.: 12/810,830

(22) PCT Filed: Dec. 12, 2008

(86) PCT No.: PCT/FR2008/001729
§ 371 (c)(1),
(2), (4) Date: Jun. 25, 2010

(87) PCT Pub. No.: WO2009/103884
PCT Pub. Date: Aug. 27, 2009

(65) Prior Publication Data
US 2010/0303778 A1    Dec. 2, 2010

(30) Foreign Application Priority Data
Dec. 26, 2007 (FR) .................................. 07 60377
Mar. 12, 2008 (FR) .................................. 08 01342

(51) Int. Cl.
*C12N 1/00* (2006.01)
*A01N 63/00* (2006.01)
*A23C 9/12* (2006.01)

(52) U.S. Cl.
USPC ................ 435/255.2; 424/93.51; 426/62

(58) Field of Classification Search
USPC ............. 424/93.51; 426/62; 435/255.1, 255.2
See application file for complete search history.

(56) References Cited

FOREIGN PATENT DOCUMENTS

| | | |
|---|---|---|
| CN | 101918536 | 12/2010 |
| EP | 1 481 682 | 12/2004 |
| EP | 1 693 064 | 8/2006 |
| FR | 20070060377 | 12/2007 |
| FR | 2928652 | 9/2009 |
| WO | WO 2006/021965 | 3/2006 |
| WO | WO 2009/103884 | 8/2009 |

OTHER PUBLICATIONS

Fangfang, Zhao, et al., "Physiological Function and Application on Cell Wall of Yeast," China Feed, Journal 17, Sep. 5, 2003, pp. 17-18.
International Search Report and Written Opinion with English Translation for PCT/FR2008/001729, Oct. 30, 2009 (mailing date), Lesaffre et Compangie, et al.
International Preliminary Report on Patentability with English Translation for PCT/FR2008/001729, Sep. 28, 2010 (completion date), Lesaffre et Compangie, et al.
Czerucka, D., et al., "Yeast as probiotics—*Saccharomyces boulardii*," Alimentary Pharmacology & Therapeutics, Sep. 2007, pp. 767-778, vol. 26, No. 6.
Dalmasso, Guillaume, et al., "*Saccharomyces boulardii* Inhibits Inflammatory Bowel Disease by Trapping T Cells in Mesenteric Lymph Nodes," Gastroenterology, Dec. 22, 2006, pp. 1812-1825, vol. 131, No. 6, Elsevier, Philadelphia, PA, USA.
Edwards-Ingram, Laura, et al., "Genotypic and Physiological Characterization of *Saccharomyces boulardii*, the Probiotic Strain of *Saccharomyces cerevisiae*," Applied and Environmental Microbiology, Apr. 2007, pp. 2458-2467, vol. 73, No. 8.

*Primary Examiner* — Blaine Lankford, Jr.
*Assistant Examiner* — Charles Zoltan Constantine
(74) *Attorney, Agent, or Firm* — Adeli & Tollen LLP

(57) ABSTRACT

The invention relates to novel yeast strains, to the yeasts resulting from these strains, to a composition containing at least one *Saccharomyces cerevisiae* yeast and/or derivatives of a yeast having a particular interest as a food additive and/or probiotic and/or functional food and/or neutraceutic and/or functional ingredient and/or cosmeceutical and/or pharmaceutical active agent. The invention also relates to the use of the same in human and/or animal nutrition, or for the treatment or prevention of inflammatory diseases.

30 Claims, 13 Drawing Sheets

PROBIOTIC YEAST COMPOSITIONS AND METHODS FOR INFLAMMATORY DISEASES

CLAIM OF BENEFIT TO PRIOR APPLICATIONS

Figure 1:
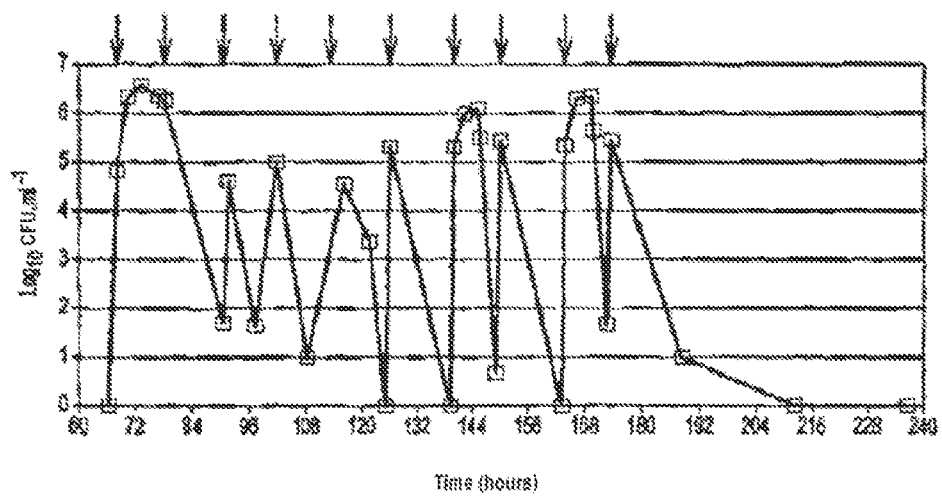

This application is a national stage application of PCT Patent Application PCT/FR2008/001729, entitled "Composition for Human and/or Animal Nutrition, Uses thereof and Yeasts," filed on Dec. 12, 2008, and now published as WO 2009/103884. PCT Patent Application PCT/FR2008/001729 claims the benefit of French Patent Application FR 0760377, filed on Dec. 26, 2007 and French Patent Application FR 0801342, filed on Mar. 12, 2008. All of the above-mentioned applications, namely PCT Patent Application PCT/FR2008/001729, published as WO 2009/103884, French Patent Application FR 0760377, and French Patent Application FR 0801342 are incorporated herein by reference.

The present invention relates to the field of human and/or animal nutrition and health.

It more particularly relates to novel yeast strains and novel yeasts obtained from the novel strains. These yeasts are notably useful for the comfort of the digestive tract and/or for preventing and/or treating disorders of the human or animal digestive tract.

Many microorganisms have already been described in the literature for their beneficial applications in humans on the digestive tract and for their nutritional benefit, as for example described in WO 2006/021965.

These microorganisms are then commonly designated by the term of probiotic which corresponds to live microorganisms capable of providing the host with a health benefit when they are administered in a sufficient amount (joint FAO/WHO Expert Consultation Probiotics in food, FAO Food and nutrition paper Nr85, ISBN 92-5-105513-0).

The benefits resulting from oral administration of the microorganisms very widely depend on the microorganism strain used, but also on its administration form. Within a same species, according to the strains used, the observed effects are indeed very fluctuating, sometimes beneficial, sometimes negative or neutral such as for example within the species *Escherichia coli* where it is possible to find both pathogenic strains (entero-toxigenic or entero-haemorrhagic types for examples) and beneficial strains such as the Nissle 1917 strain (M. de Vrese; P. R. Marteau. *Probiotics and Prebiotics: Effects on Diarrhea*, 2007, J. Nutr., 137(3 Suppl. 2), 803S-811S). It is thus presently impossible to predict for a given strain whether a benefit in terms of human health from the administration of this strain may be reckoned with, nor even to predict the nature of its possible benefit or its intensity.

A certain number of strains of microorganisms, notably among yeasts and lactic bacteria, have already been identified for certain beneficial effects on the gastro-intestinal tract. Nevertheless, obtaining complete beneficial action on the gastro-intestinal tract often requires concomitant administration of several strains of different nature (I. Goktepe; V. K. Juneja; M. Ahmedna (eds.) *Probiotics in Food Safety and Human Health* 2006, CRC Taylor & Francis, ISBN 1-57444-514-6).

Further, it has been observed that a large number of microorganisms, in particular lactic bacteria, have pro-inflammatory action. This pro-inflammatory effect may prove to be particularly detrimental and undesirable, for example in auto-immune diseases or immune deficiencies.

Certain fractions of yeasts and/or derivatives of yeasts have been described for their beneficial effect on the digestive tract.

Thus, mannoproteins derived from yeasts have been described for their effect of inhibiting adhesion of pathogens. Also, the walls of yeasts have been described for their fiber effect. However, there exists many strains of *Saccharomyces cerevisiae* yeasts and, they do not all have beneficial effects or the same effects.

Further, depending on the strains used and the administered yeast forms, the effects may also be very variable.

Also, there subsists the need for being able to have novel strains of microorganisms which may exert a beneficial effect on health preventively and/or curatively on either specific pathologies or dysfunctions or not, or on both physical and psychic general health condition.

The object of the invention is therefore a novel strain of *Saccharomyces cerevisiae* deposited at the Collection Nationale de Cultures de Microorganismes under No. CNCM I-3856, and a novel strain of *Saccharomyces cerevisiae* var. *boulardii* deposited at the Collection Nationale de Cultures de Microorganismes under No. CNCM I-3799.

Its object is also a *Saccharomyces cerevisiae* yeast obtained from the strain deposited at the Collection Nationale de Cultures de Microorganismes under No. CNCM I-3856, and a *Saccharomyces* var. *boulardii* yeast obtained from the strain deposited at the Collection Nationale de Cultures de Microorganismes under No. CNCM I-3799.

Another object of the invention is a composition comprising a *Saccharomyces cerevisiae* yeast obtained from the strain deposited at the Collection Nationale de Cultures de Microorganismes under No. CNCM I-3856 and/or a *Saccharomyces* var. *boulardii* yeast obtained from the strain deposited at the Collection Nationale de Cultures de Microorganismes under No. CNCM I-3799 and/or at least one *Saccharomyces cerevisiae* yeast derivative selected from yeast extracts, wall derivatives, parietal glucans, parietal mannoproteins, yeast lipid fractions, yeast nucleic acid (RNA, DNA) fractions.

The composition according to the invention has the following advantages:
- capability, in particular in its dry forms, of resisting and surviving upon passing through the gastric barrier, which allows optimization of its effects on the gastro-intestinal tract;
- anti-inflammatory action;
- absence of any pro-inflammatory effect or a very small effect;
- capability of reducing intestinal pains, and finally
- capability of preventing and reducing adhesion and colonization by pathogenic bacteria and/or those with invasiveness of the gastro-intestinal tract, in particular of the small intestine and the of the colon.

Such a novel composition, having this combination of features, has never been described or identified yet.

It therefore has exceptional interest.

Another object of the invention is a use of the previous composition for preparing a food supplement and/or probiotic and/or functional food and/or nutraceutical and/or functional ingredients and/or cosmeceutical and/or pharmaceutical active ingredient, intended for humans and/or animals.

Moreover the invention relates to a use of the composition as defined earlier for the preparation of food compositions intended to improve gastro-intestinal comfort and/or improve intestinal flora.

The object of the invention is also a use of the composition as defined earlier for preparing a drug intended for treating and/or preventing intestinal disorders, intestinal functional disorders or gastro-intestinal diseases.

An object of the invention is a use of the composition as defined previously for preparing a drug intended for treating and/or preventing pathologies or disorders of the intestine indicated by a condition of hyperalgesia.

Finally, a last object of the invention is a kit comprising at least one yeast and/or at least one yeast derivative as defined earlier in a form suitable for oral administration.

The strain, deposited by the Applicant, under the Treaty of Budapest at the Collection Nationale de Cultures de Microorganismes (Institut Pasteur Paris) under No. CNCM I-3856, will be called "ScPro1" with the purpose of conciseness.

The strain, also deposited by the Applicant under the Treaty of Budapest at the Collection Nationale de Cultures de Microorganismes (Institut Pasteur Paris) under No. CNCM I-3799, will be designated as "SCBI" with a purpose of conciseness.

Finally, with a last purpose of conciseness, the *Saccharomyces cerevisiae* yeast derivative selected from the yeast extracts, the wall derivatives, the parietal glycans, the parietal mannoproteins, the yeast lipid fractions, the yeast nucleic acid (RNA, DNA) fraction and their mixtures, will be designated as "derivative".

Probiotic is meant to designate live microorganisms which, they are integrated in a sufficient amount, exert a positive effect on health, comfort and wellness beyond traditional nutritional effects.

By nutritional food or nutraceutical or functional food or cosmeceutical, is meant a foodstuff which contains ingredients having beneficial effects for health or capable of improving physiological functions.

By food supplement, is meant a foodstuff having the purpose of completing normal food diet. A food supplement is a concentrated source of nutrients or other substances having a nutritional or physiological effect, when they are taken alone or as a combination in small amounts.

By foodstuffs intended for particular feeding (DDAP), is meant a foodstuff having a particular nutritional goal, intended for a well-defined population group, such as infants, toddlers, sportsmen.

The food composition as mentioned in the invention may be a food supplement or a DDAP.

The strains of the invention were identified by the Applicant for their many advantages and notably for their capability of inducing beneficial effects on the human digestive tract, in particular the small intestine, and the colon, but also on the body generally.

Indeed, it was observed that surprisingly the yeast ScPro1 and/or SCBI and/or derivative is capable of inducing an anti-inflammatory action, unlike a great number of yeast strains, and this without any pro-inflammatory effect.

Indeed, the ScPro1 and/or SCBI yeast and/or derivative causes increase in the secretion of the interleukin IL-10 involved in anti-inflammatory signals.

Further, unlike the actions of probiotic bacteria of the lactobacilli type, the ScPro1 and/or SCBI strain and/or derivative does not induce the synthesis of pro-inflammatory cytokine IL-12. Also, the production of TNFα and IFNγ pro-inflammatory cytokines is markedly lower relatively to bacterial probiotics. Tests have moreover allowed demonstration of the anti-inflammatory effect in vivo of this yeast ScPro1, notably a decrease by half of the inflammation of the large intestine and a reduction by one third of intestinal necrosis.

Further, the ScPro1 and/or SCBI yeast and/or derivative, in its dry forms, is capable of crossing the gastric barrier without any negative impact on its survival or its integrity and this yeast does not settle in a colic environment.

The Applicant demonstrated for the first time and particularly surprisingly, that the ScPro1 and/or SCBI yeast and/or derivative is capable of increasing resistance to pain, notably on a rat model in vivo.

In addition to these beneficial effects, this ScPro1 and/or SCBI yeast and/or derivative is capable of inhibiting colonization and/or invasion of pathogenic microorganisms and/or those with invasiveness at the intestine. Administration of this yeast causes a decrease of the enterobacteria at the colon and of intestinal flora resistant to antibiotics.

In particular, it has shown a prophylactic and therapeutic capability against intestinal colonization by *Candida albicans* and inflammations caused and sustained by this pathogen. Moreover, this yeast has an inhibitory effect on the power of adhesion and of invasion of pathogenic strains and/or those with invasiveness of *Escherichia coli* pathogenic types isolated from ileal biopsies from patients affected with Crohn's disease.

According to the present invention, this ScPro1 and/or SCB1 yeast and/or derivative may be administered in a live or viable form, preferably orally.

By "live form" or "live" is meant according to the invention, a yeast, the metabolism of which is active or reactivatable or capable of multiplying. This is notably yeast in a dry form or in a fresh form.

Typically, the yeast in a fresh form appears as a pressed or crumbled yeast. It may also appear as a yeast suspended in an aqueous phase and it is then referred to as liquid yeast. In this case, the yeast will preferably be encapsulated. The encapsulation methods and the different types of capsules are well-known to one skilled in the art.

Among the dry yeast forms, mention may be made of the yeast which may appear in an instantaneous dry or active dry form. By dry yeast is meant any yeast having a dry material level above 90%, preferably ranging from about 92%-96%.

Among dry yeasts, mention may further be made of yeasts with intermediate humidity, either deep-frozen or not.

Instantaneous dry yeast is mainly intended for industrialists and master bakers. Other applications and outlets are possible on the basis of food reference systems (pharmacy, alcoholic fermentation). The particularity of this dry yeast is that it does not need rehydration before being incorporated into the flour.

It stems from dehydration of the yeast by the action of a hot air gradient which allows transformation of a pasty product (pressed or liquid yeast) into thin dry vermicelli while remaining active. The product should then, for it to remain stable, be conditioned in the absence of oxygen.

The active dry yeast is live yeast, dried at low temperature in order that it retains its fermenting power and is provided with very long preservation. It appears as spherules.

This yeast stems from dehydration of the yeast by joint action of heat and of mechanical activity which allows transformation of the yeast in a pasty form into a dry product while sparing its viability.

The selected active yeasts are obtained by extrusion and drying in a fluidized bed of biomass (live yeast cells). This active dry yeast, i.e. a dry yeast having a high content of live yeast cells, appears as granules generally with a diameter from 0.1 μm to 2.5 mm, and a $H_2O$ content of 4-8% by mass.

These dry forms have the advantage of providing better gastro-resistance as compared with the fresh form and optimizing beneficial effects of the yeast according to the invention. According to the invention, the yeast according to the invention will preferentially be in the form of active dry yeast.

It is generally recognized that pro-inflammatory cytokines stimulate the inflammatory mechanisms which may then be responsible for a large number of clinical problems, in particular in the case of auto-immune diseases, or immune deficiencies.

Thus, the yeast according to the present invention may be used for preventing and/or treating diseases or inflammatory disorders of the intestine, whether they are chronic or acute, either possibly associated or not with diarrheas or constipations.

In a first embodiment, the disorders and diseases are either associated with diarrheas or not.

In a second embodiment, the disorders and diseases are not associated with diarrheas. Notably the ScPro1 and/or SCB1 yeast and/or derivative may be useful for preventing or treating colitises which are essentially characterized by inflammation of the colon.

In particular, this yeast is well adapted to preventing and/or treating Chronic Inflammatory Bowel Diseases (CIBD), notably ulcerative colitis, hemorrhagic rectocolitis, celiac diseases or Crohn's disease.

These diseases are notably characterized by an exacerbated immune response in which are involved multiple inflammatory cascades. Thus, within the scope of preventing or treating these diseases with a probiotic and/or a medical food and/or a functional food and/or a nutraceutical and/or a cosmeceutical, it is important that the pro-inflammatory effects be as weak as possible.

The ScPro1 and/or SCB1 yeast and/or derivative according to the invention is therefore most particularly suitable for these uses. This yeast has several additional advantages.

The first is that it has the capacity of increasing resistance to pain. The second, notably for Crohn's disease, is that this yeast is notably capable of inhibiting the adhesion and invasion power of $E.\ coli$ pathogenic strains and/or those with invasiveness from patients suffering from this disease.

The inflammatory response may notably due to the invasion of all the pathogenic microorganisms.

Thus, the ScPro1 and/or SCB1 yeast and/or derivative according to the invention shows good effectiveness for preventing or treating gastro-intestinal disorders or diseases due to the colonization of the intestines by pathogenic microorganisms and/or those with invasiveness, prokaryotes, such as bacteria, or eukaryotes, such as fungi.

Gastro-intestinal disorders or diseases may be intestinal chronic inflammatory diseases such as ulcerative colitis, celiac disease, Crohn's disease, and hemorrhagic rectocolitis.

Moreover, the ScPro1 and/or SCB1 yeast and/or derivative allow increase in the resistance to pain, it also has an advantage in the preventive or curative treatment of bowel pathologies or disorders characterized by a state of hyperalgesia. These pathologies or disorders may notably be functional intestinal disorders, chronic inflammatory bowel diseases (CIBD), or food intolerances (allergies, conditionings, etc. . . . ) characterized by chronic visceral pain.

It is particularly adapted to preventive or curative treatment of hyperalgesias and in particular of the irritable bowel syndrome (IBS) regardless of its form (constipation, diarrhea or a combination of both), but also of chronic visceral pains which do not enter the scope of IBS, such as functional abdominal pains without any fecal elimination disorder (FAPS: Functional Abdominal Pain) and pains related to food intolerances and to the celiac disease.

The ScPro1 and/or SCB1 yeast and/or derivative or any composition comprising it, may therefore be used preventively in subjects having predispositions or sensitivity to this type of disorders or diseases, or curatively, for example during bouts or over longer periods. The composition and method of the invention may reduce suffering of the subjects, alleviate symptoms or the cause of these disorders.

The conjunction of the effects of this yeast and/or derivative according to the invention on pain, inflammation and pathogenic microorganisms and/or those with invasiveness certainly causes improvement in wellness, in health and/or in comfort of the human or animal gastro-intestinal tract.

The composition according to the invention may comprise a ScPro1 yeast and/or an SCB1 yeast and/or at least one derivative of *Saccharomyces cervevisiae* yeast selected from yeast extracts, wall derivatives, parietal glucans, parietal mannoproteins, yeast lipid fractions, yeast nucleic acid (RNA, DNA) fractions in an amount ranging from about between $10^7$ and $6 \cdot 10^{10}$CFU, and preferably between $10^8$ and $2 \cdot 10^{10}$CFU, or, between 1 mg and 10 g, and preferably between 1 mg and 1 g. This amount may be a daily amount taken once or in several times during the day.

Preferentially, the ScPro1 and/or SCB1 yeast and/or derivative is used in therapeutic or non-therapeutic applications in a daily dose comprised between $10^7$ and $6 \cdot 10^{10}$CFU (Colony-Forming Units), and preferably between $10^8$ and $2 \cdot 10^{10}$CFU.

In the case when the yeast and/or derivative is in a live form but non-viable, the useful daily dose in therapeutic or non-therapeutic applications will preferably be comprised between 1 mg and 10 g, preferably between 1 mg and 1 g. The daily effective dose may be administered in one, two, three or four takings.

The yeast and/or derivative according to the invention or the compositions comprising it, are preferably administered orally. It may be administered in a therapeutically effective amount, which means that at least one of the symptoms is reduced or suppressed.

The ScPro1 and/or SCB1 yeast and/or derivative may be included in a human or animal food composition and/or administered with excipients or carriers suitable for oral administration.

The composition intended for human food may be a liquid, a paste or a solid. Notably, the composition may be a dairy product such as cheese, butter, yogurt or cream, a fruit-based product such as fruit juice, compote or fruit jelly, a drink or solid foodstuff, for example a snack, a biscuit or other food. Thus, the composition comprises the ScPro1 and/or SCB1 yeast and/or derivative and the components of the foodstuff or of the drink.

The ScPro1 and/or SCB1 yeast and/or derivative may also be included in a pharmaceutical composition. The pharmaceutical composition is adapted to oral administration. It therefore comprises the ScPro1 and/or SCB1 yeast and/or derivative as well as an adequate conventional carrier selected from authorized excipients for the manufacture of pharmaceutical preparations. It may be formulated as a liquid, such as a syrup or a phial, or as tablets, gelatin capsules, sachets, capsules or powder or other suitable galenic forms.

The ScPro1 and/or SCB1 yeast and/or derivative may further be administered with other probiotics and/or other functional ingredients, in particular probiotic bacteria notably for still more complete preventive action.

As an example, mention may be made of lactic bacteria of the genera *Lactobacillus, Bifidobacterium, Pediococcus, Propionibacterium*, or *Leuconostoc*.

The ScPro1 and/or SCB1 yeast and/or derivative may also be administered with other active ingredients such as antibiotics, analgesics, anti-diarrheal agents, laxatives, and mixtures thereof.

Figure 2:
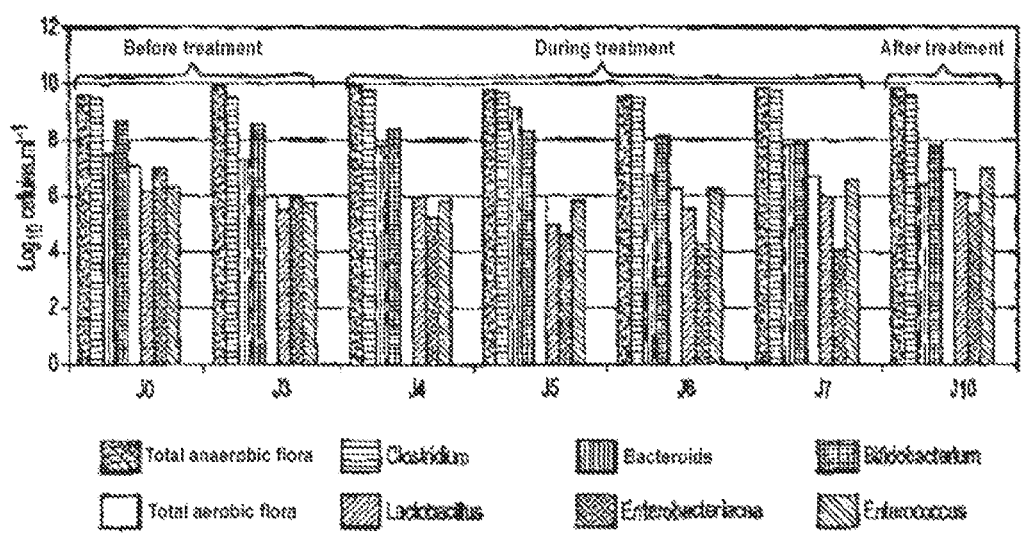
Figure 3:
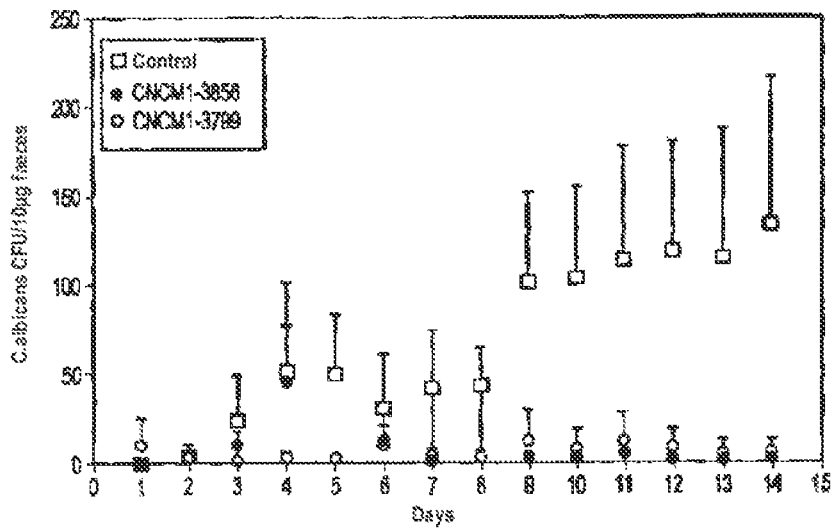
Figure 4:
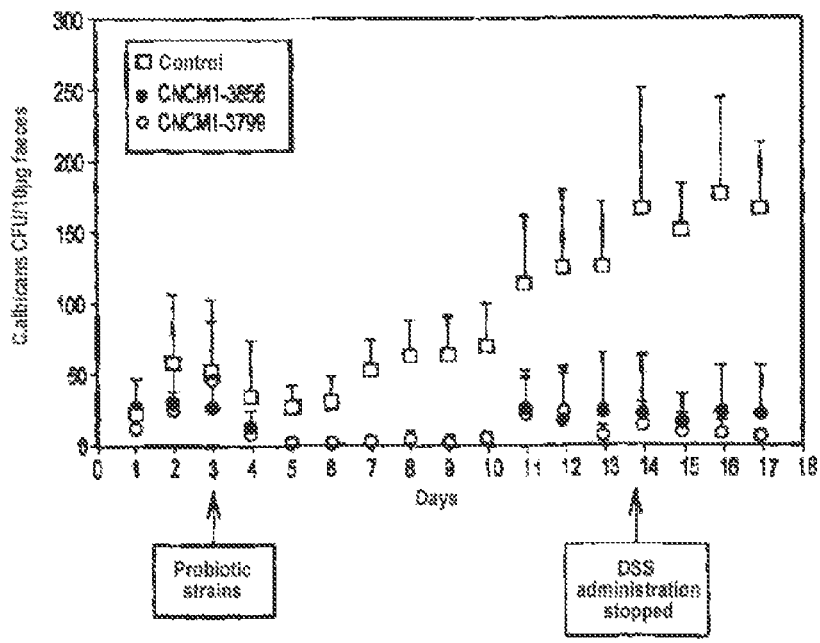
Figure 5:
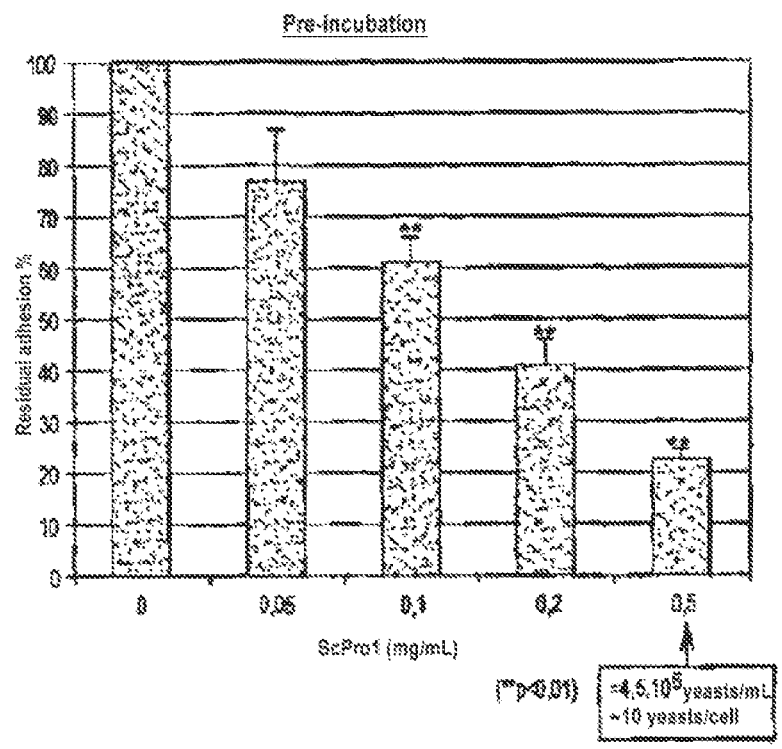
Figure 6:
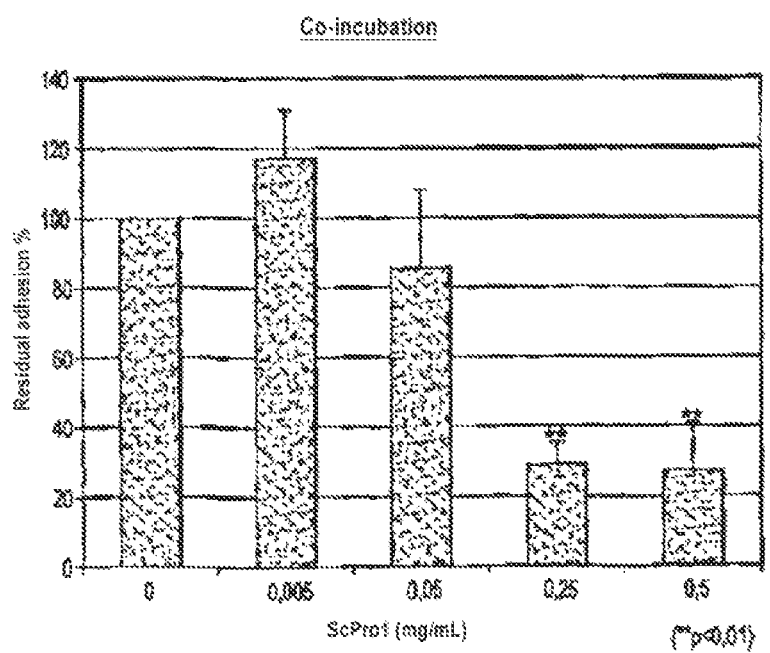
Figure 7:
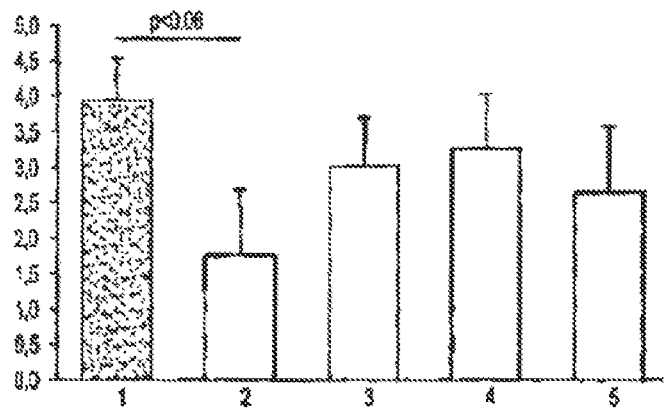
Figure 8:
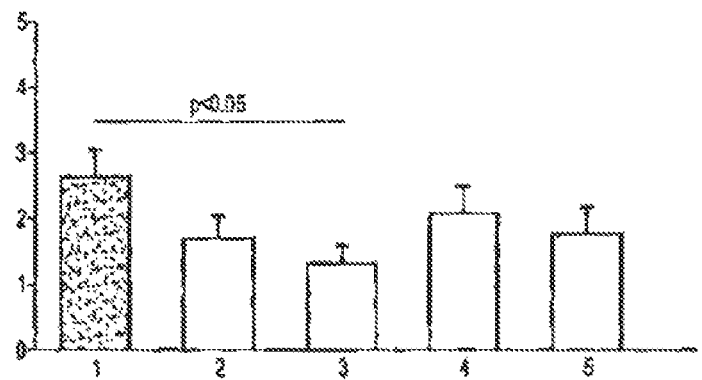
Figure 9:
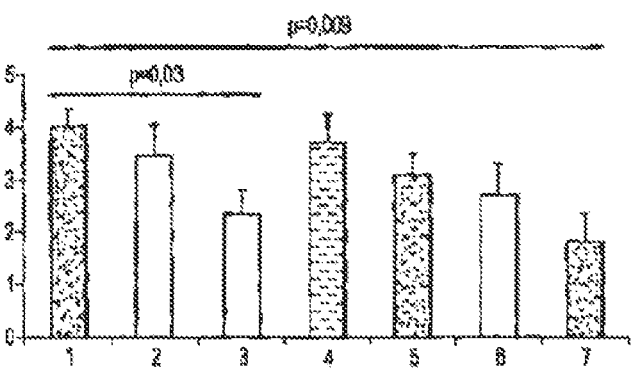
Figure 10:
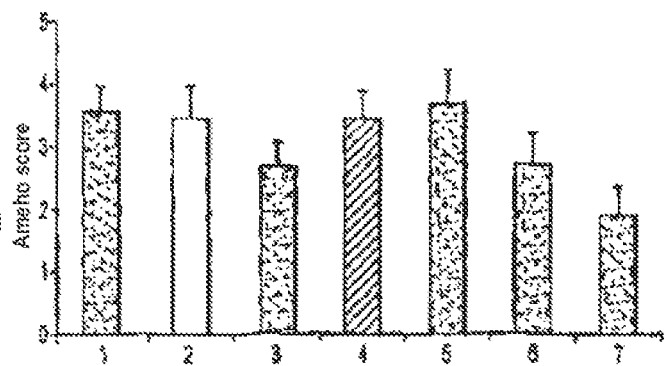
Figure 11:
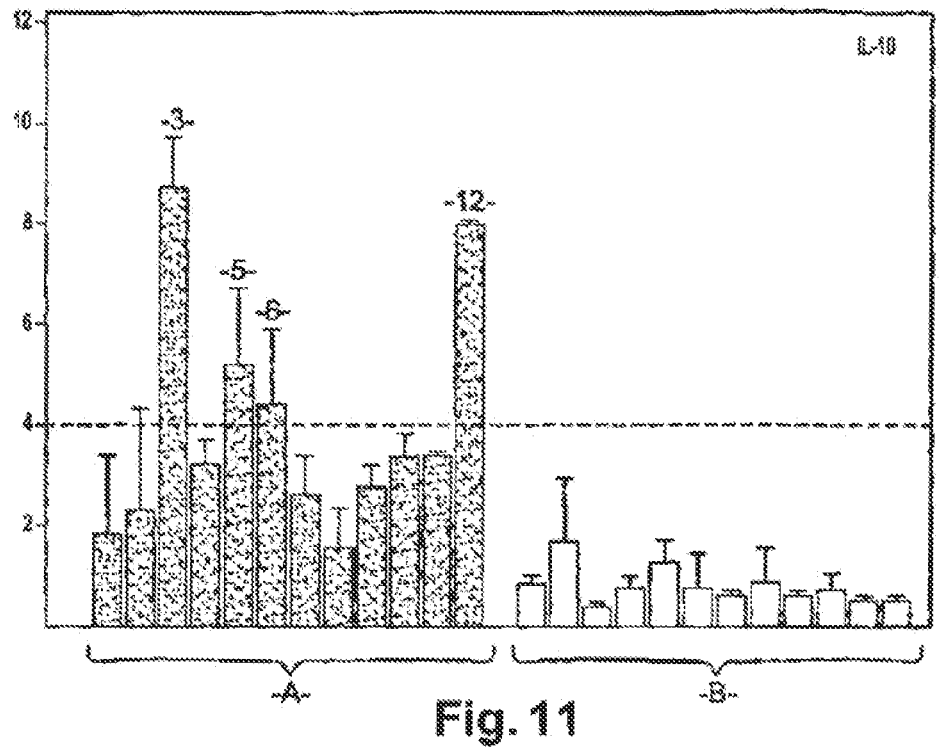
Figure 12:
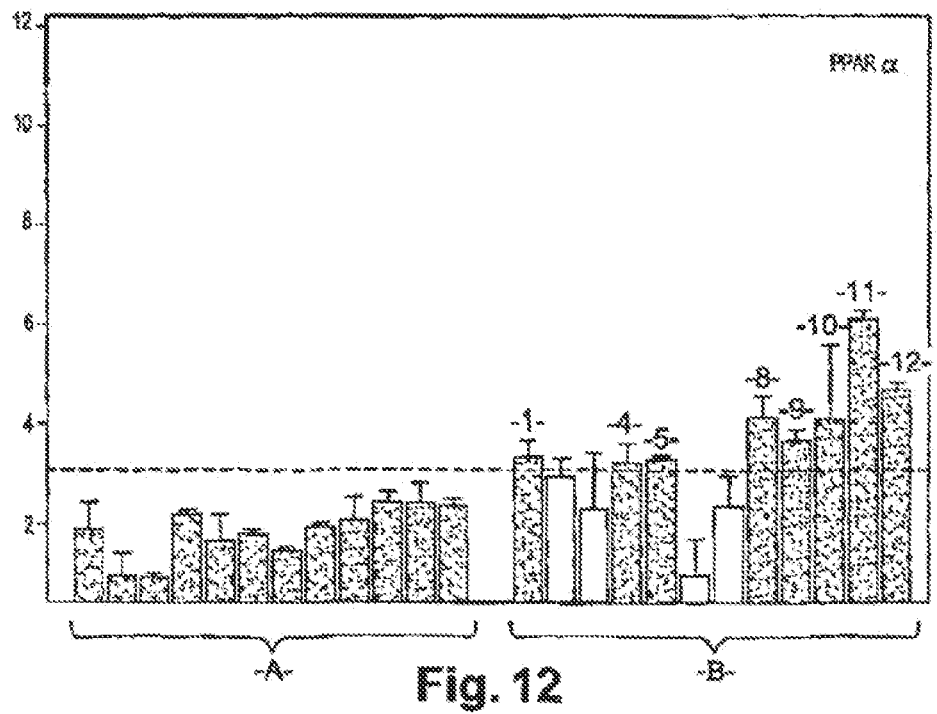
Figure 13:
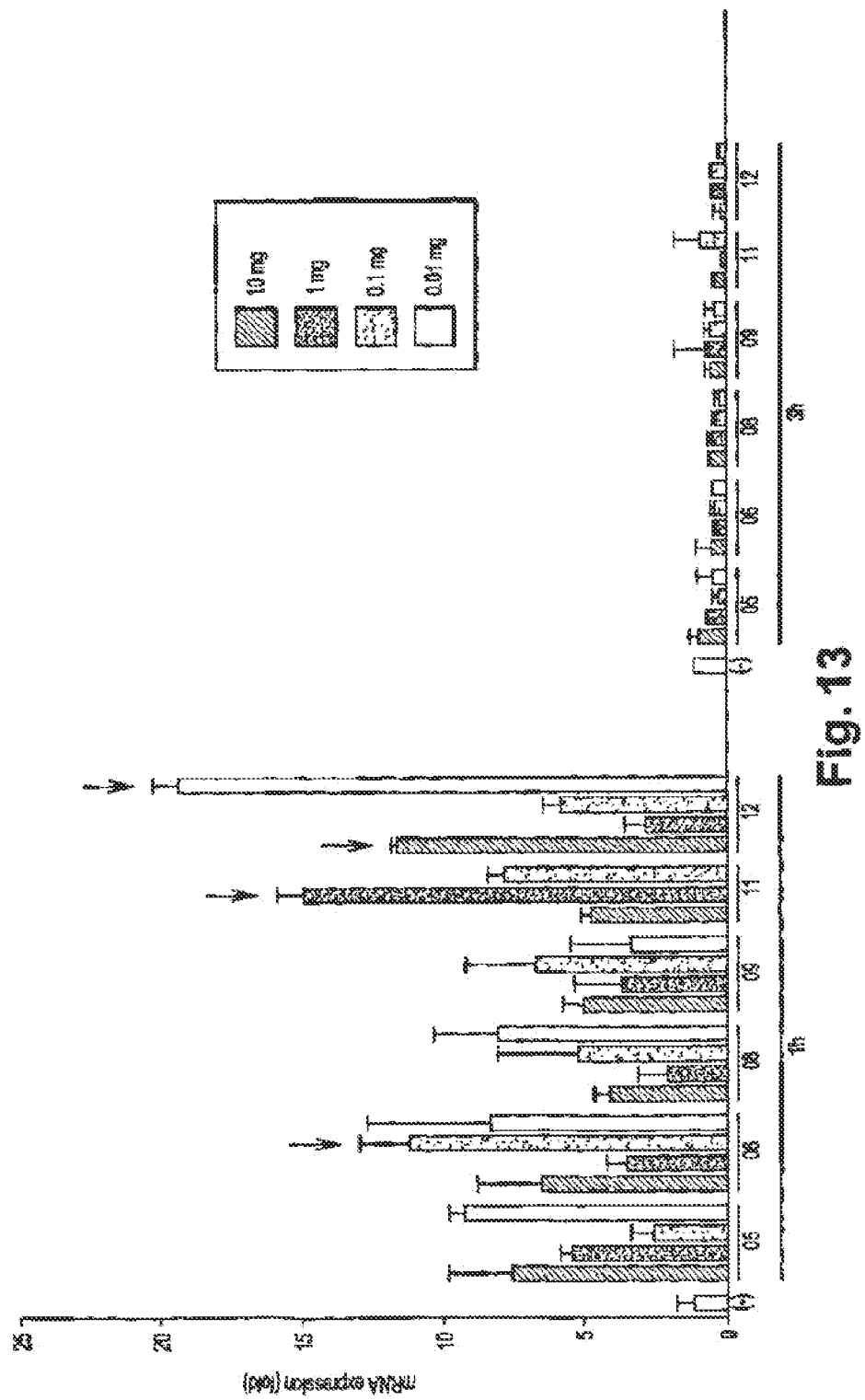
Figure 14:
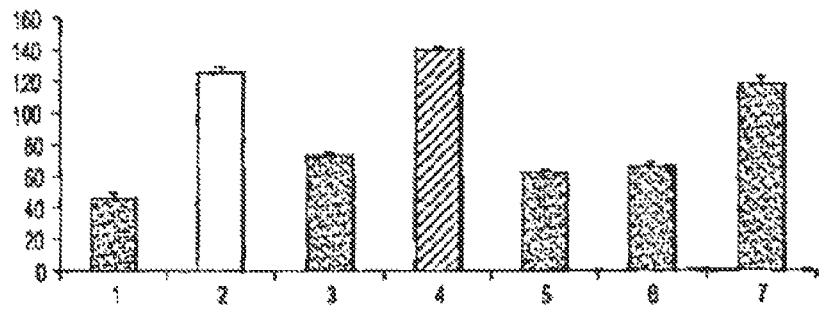
Figure 15:
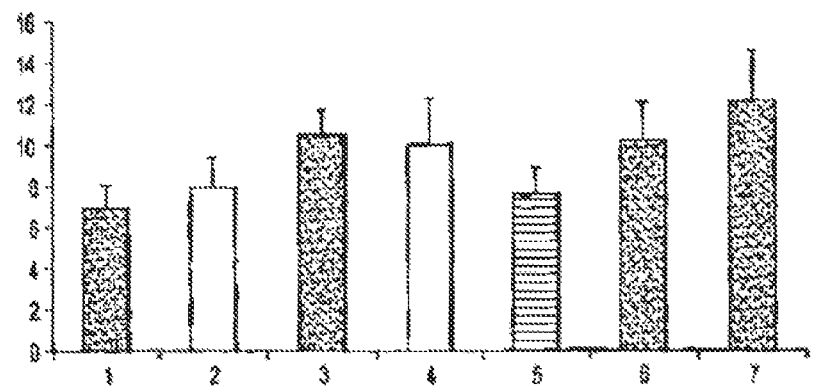
Figure 16:
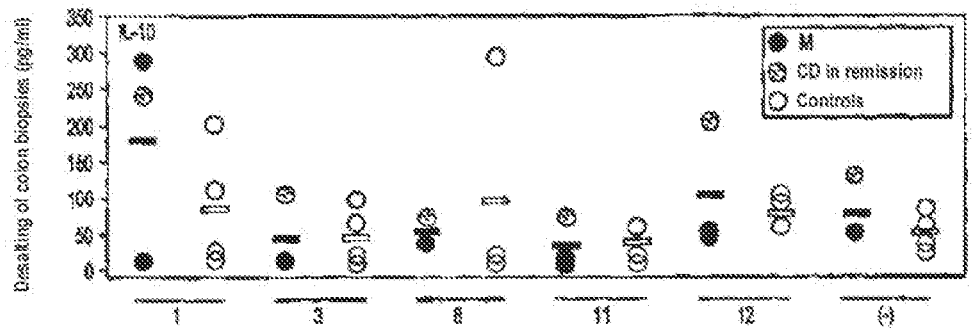
Figure 17:
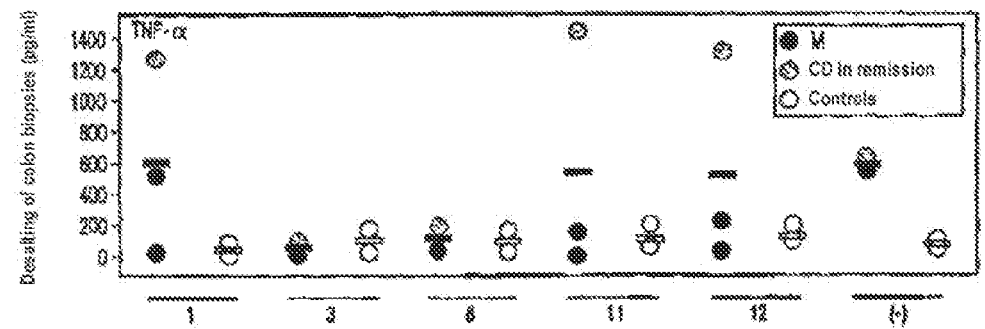
Figure 18:
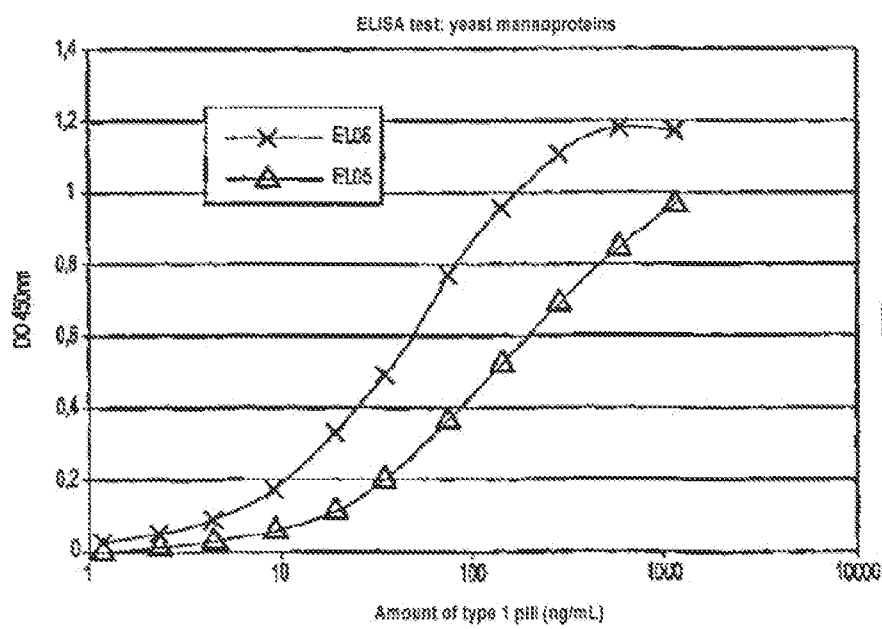
Figure 22A:
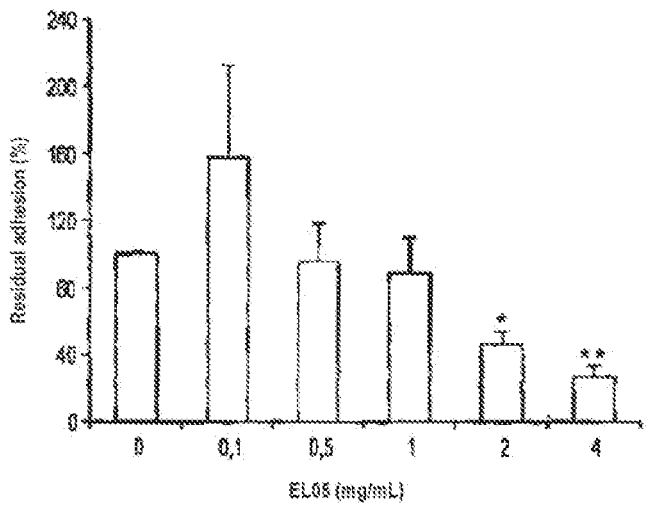
Figure 22B:
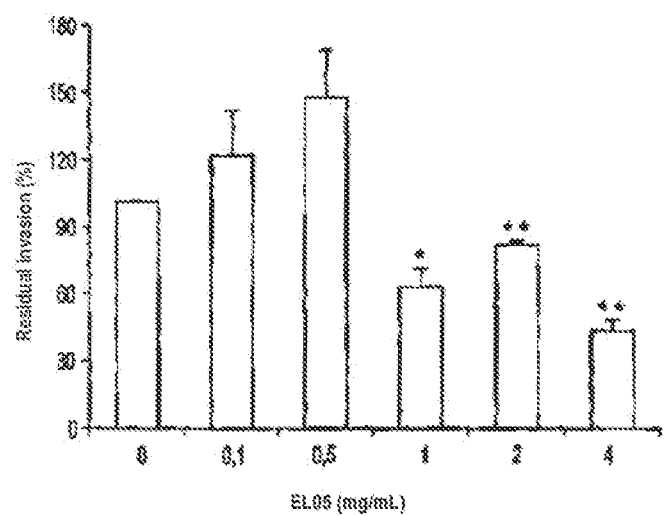
Figure 23:
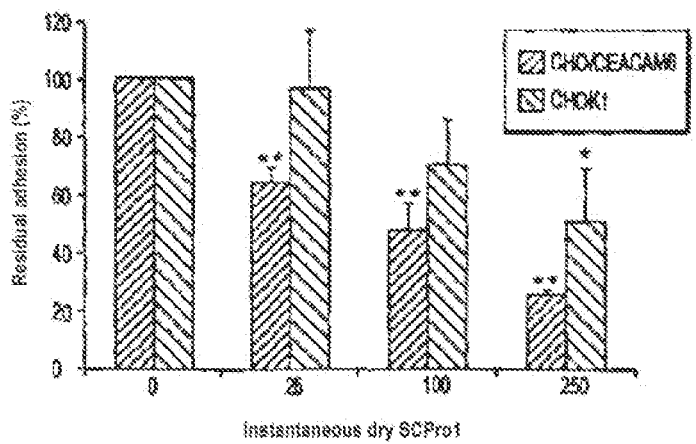
Figure 24:
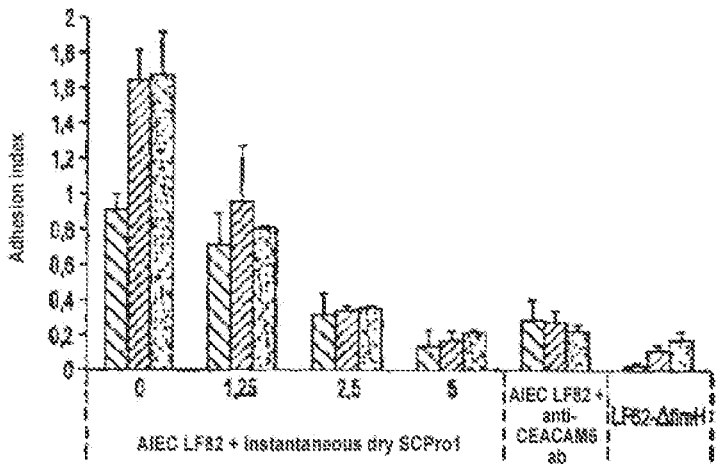
Figure 25:
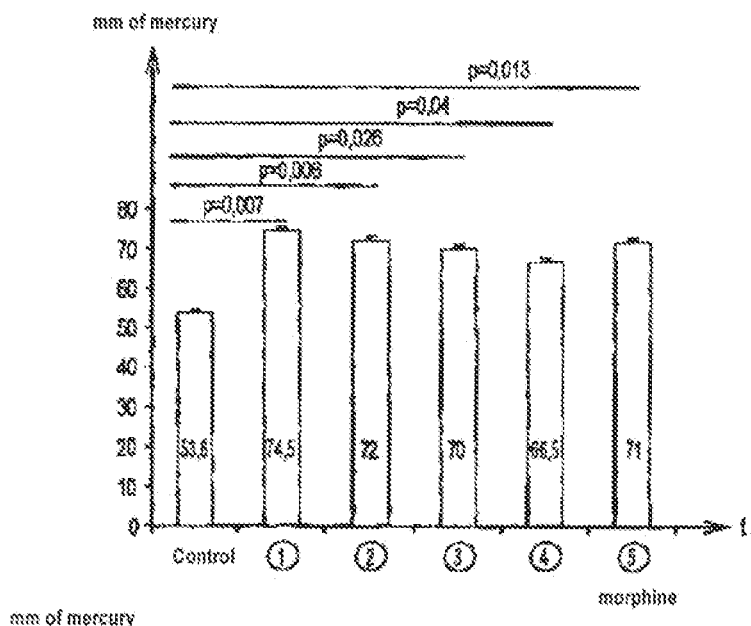
Figure 26:
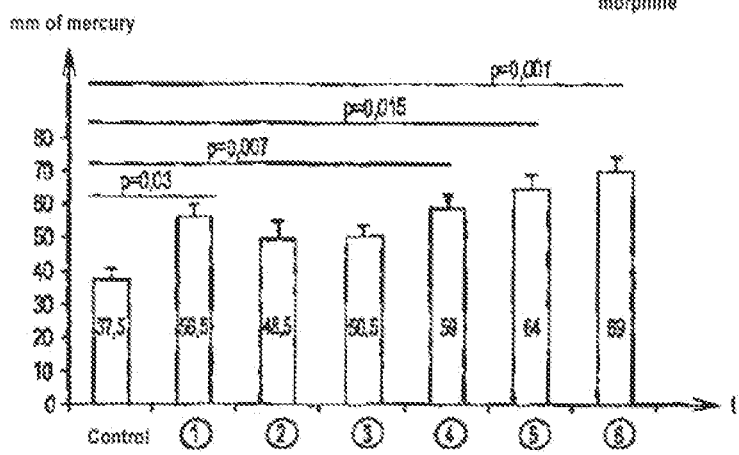

The present invention will now be illustrated with examples and figures which follow, which are given as an illustration, which are by no means limiting and wherein:

FIG. 1 illustrates the monitoring of the survival of the ScPro1 yeast in an artificial digestive system simulating the human colon, according to Example 2, FIG. 2 illustrates the effects of the ScPro1 yeast on colic microflora, according to Example 2, FIGS. 3 and 4 illustrate the evolution of the number of cells of *Candida albicans* in mice stools for the experiments 1 and 2 of Example 5 corresponding to the prophylactic (FIG. 3) and curative (FIG. 4) models, FIG. 5 illustrates the percentage of residual adhesion of *Escherichia coli* AIEC LF82 cells to human intestinal epithelial cells depending on the amount of ScPro1 yeast with pre-incubation; the yeast cells were incubated with intestinal epithelial cells for one hour. The infection of the cells with the strain AIEC LF82 was carried out in the presence of the ScPro1 yeast, according to Example 6, FIG. 6 illustrates the percentage of residual adhesion of *Escherichia coli* AIEC LF82 cells to human intestinal epithelial cells depending on the amount of ScPro1 yeast with co-incubation; the yeast cells and the *Escherichia coli* cells were incubated simultaneously with the intestinal epithelial cells for one hour according to Example 6, FIG. 7 illustrates the estimation of the intensity of the inflammation of mice intestines according to the macroscopic Wallace score after administration of ScPro1 and SCB1 yeast, according to Example 4, FIG. 8 illustrates the estimation of the intensity of the inflammation of the intestinal epithelium of mouse intestine according to the histological Ameho score after administration of ScPro1 and SCB1 yeasts, according to Example 4, FIG. 9 illustrates the estimation of the intensity of the inflammation of mouse intestines according to the macroscopic Wallace score after administration of the ScPro1 and SCB1 yeasts taken alone or as a combination, according to Example 4, FIG. 10 illustrates the estimation of the intensity of the inflammation of mouse intestinal epithelium according to the histological Ameho score after administration of the ScPro1 and SCB1 yeasts, taken alone or as a combination, according to Example 4, FIG. 11 illustrates the mRNA expression level of the gene coding for the IL-10 protein, one hour, and three hours after putting the yeasts or derivatives according to the invention in contact with human intestinal epithelial cells according to Example 7, FIG. 12 illustrates the mRNA expression level of the gene coding for the nuclear receptor PPARα, one hour after, and three hours after putting the yeasts or derivatives according to the invention in contact with human intestinal epithelial cells according to Example 7, FIG. 13 illustrates the modulation of the mRNA expression of the gene coding for the IL-10 protein after one hour, and after three hours after putting the yeast derivatives according to the invention in contact with human intestinal epithelial cells according to Example 7, FIG. 14 illustrates the expression of the gene coding for the IL-10 protein in mouse intestinal epithelial cells after administration of the yeast and/or derivative according to the invention (Example 4), FIG. 15 illustrates the expression of the gene coding for the nuclear receptor PPARα in mouse intestinal epithelial cells after administering a yeast and/or derivative according to the invention (Example 4), and FIG. 16 shows the secreted amounts of cytokine IL-10, measured in pg/mL, by the intestinal cells from biopsies of patients either affected with Crohn's disease or not after putting them into contact with the yeasts and derivatives according to the invention (Example 8), FIG. 17 shows the amounts of TNF-α cytokine, measured in pg/mL, secreted by the intestinal cells from biopsies of patients either affected with Crohn's disease or not after their putting them into contact with yeasts and/or derivatives according to the invention (Example 8), FIG. 18 shows the result of the test for determining the binding capacity of type 1 pili on mannoprotein fractions (EL 05 and EL 06) of ScPro1 yeast, FIGS. 19A and 19B respectively show the mean residual invasion and adhesion percentages of the AIEC LF82 strain relatively to T84 cells, during co-incubation with increasing yeast concentrations (Example 6)—* $p<0.05$, ** $p<0.01$, FIGS. 20A and 20B respectively show the mean invasion and adhesion percentages of the AIEC LF82 strain relatively to T84 cells during co-incubation with increasing concentrations of EL05 yeast mannoproteins—(Example 6), FIGS. 21A and 21B respectively show, the mean residual invasion and adhesion percentages of the AIEC LF82 strain relatively to T84 cells during pre-incubation with increasing concentrations of yeast (Example 6)—* $p<0.05$, and ** $p<0.01$, FIGS. 22A and 22B respectively show the mean invasion and adhesion percentages of the strain AIEC LF82 relatively to T84 cells during pre-incubation with increasing concentrations of EL05 yeast mannoproteins (Example 6)—* $p<0.05$, and ** $p<0.01$, FIG. 23 shows the residual adhesion percentages of the AIEC LF82 strain relatively to CHO-K1 and CHO-K1/CEACAM6 cells, during pre-incubation with increasing concentrations of instantaneous dry ScPro1 yeast (Example 6)—* $p<0.05$, and ** $p<0.01$, FIG. 24 shows the adhesion of the AIEC LF82 strain or of the non-piliated LF82-δfimH mutant to the brush border of enterocytes of 3 samples of cells affected with Crohn's disease (Example 6), FIG. 25 shows the measurement of the pain perception thresholds (measured in mm of mercury) relatively to different yeasts on healthy rats, (Example 9), and FIG. 26 shows the measurement of the pain perception thresholds (measured in mm of mercury) relatively to the different yeasts on rats having visceral hypersensitivity (Example 9).

EXAMPLES

Example 1

Survival of the ScPro1 and/or SCB1 Yeast in an Artificial Digestive Environment Simulating Human Intestine Study of the Fate of the ScPro1 and/or SCB1 Yeast During Gastro-Intestinal Transit The ScPro1 and/or SCB1 yeasts were tested and studied in vivo in an artificial digestive environment simulating human digestion and notably by studying the survival of tested viable yeasts during gastro-intestinal transit.

Two samples of the active dry yeast form ScPro1 and two samples of the active dry yeast form SCB1 were tested.

Both samples are differentiated by the storage time at room temperature in vacuo: either aging of less than 6 months or 2 year aging.

Experimental Conditions:

The digestions were carried out in the system called TIM1 (stomach+small intestine), according to experimental conditions established from data from the literature and reproducing the digestion of a liquid foodstuff (water) in a healthy human adult with an empty stomach, with removal of the digestion products by dialysis and absorption. Each digestion was conducted over 5 hours. All the digestions were carried out under the same general operating conditions, i.e.:

Temperature: the temperature was 37° C.

Gastric emptying parameters: gastric emptying follows the law defined by Elashoff et al. (1982) stated as:

$$F=t2e\{-(1/T)^b\}$$

wherein F illustrates the delivered meal fraction, t is the time, T is the time for half-emptying the foodstuff and b is a parameter describing the aspect of the curve. The parameters are T=15 min; b=1. Ileal emptying parameters: ileal emptying follows the modified Elashoff law (introduction of a parameter d allowing the emptying to be slowed down at the end of the digestion, $F_m=F+d*t^3$). The parameters are: T=150 min; b=2.4; d=$-10^{-7}$ (cf. FIG. 2).

pH set values:

Stomach (min/pH): 0/6.0; 10/3.2; 20/2.4; 40/1.8; 60/1.6; 90/1.5; 300/1.5

Duodenum: 6.4

Jejunum: 6.9

Ileum: 7.2

Gastric secretions:

HCl

Pepsin

Lipase

Intestinal secretions:

$NaHCO_3$ in the three parts of the small intestine

Bile extract in the duodenum

Pancreas extract in the duodenum

Dialysis/Absorption:

Removal of the "small" molecules of the intestinal chyme was carried out at two levels of the TIM1 (jejunum and ileum) with hemodialyzers. Dialysis of the intestinal chyme was carried out continuously against a saline solution, the composition of which was close to that of blood plasma. The dialysates were collected in dialysis bags.

Samples were taken during the digestion at different levels of the tract in order to monitor the survival of the tested yeasts.

Counts of yeasts were performed according to standard microbiological methodologies and were carried out on the taken samples in the stomach at 10, 20, 30 and 45 min, in the ileal outlets cumulated over periods of one hour, and in the final residue.

The counting method was the following:

Each sample was rapidly subject to serial dilution to one tenth in sterile physiological saline (NaCl 8.5 g/L). And then 0.1 mL of each dilution was deposited and spread out on the surface of a gelose medium distributed in Petri dishes (two dishes per dilution). The dishes are incubated for 48 hrs at 35° C. before proceeding with the counting of the "Colony-Forming Units" (CFU).

The result of the counts was expressed in CFU/mL (raw data) and as a percentage of the live yeast cells relatively to the number of initially introduced yeasts, in order to determine the survival rates of the yeasts in the stomach and upon exiting the small intestine.

The following table summarizes the theoretical (if 100% viability) and real survival rates obtained for each strain at the stomach, at the whole of the ileal outlets after 5 hrs of digestion, and at the whole of the system after 5 hrs of digestion.

Results:

| Digested products | Introduced yeasts in CPU | Stomach outlet at T = 45 min | Ileal outlet at T = 5 hrs | Overall survival at T = 5 hrs |
|---|---|---|---|---|
| ScPro1 batch 1 | 3.5 $10^{10}$ | 89% | 100% | 106% |
| ScPro1 batch 2 | 2.0 $10^{10}$ | 88% | 95% | 106% |
| SCB 1 | 1.5 $10^{10}$ | 83% | 76% | 81% |
| SCB 2 | 1.5 $10^{10}$ | 85% | 69% | 76% |

Conclusion These results actually demonstrate excellent gastro-intestinal survival for the ScPro1 and SCB1 yeasts.

Example 2

Survival of the ScPro1 Yeast in an Artificial Digestive Environment Simulating the Human Intestine Study of the Survival of ScPro1 Yeasts During Colic Fermentation and their Influence on Intestinal Microflora The ScPro1 yeast in an active dry form was tested and studied in vitro in an artificial digestive environment simulating human digestion and notably by studying the fate and the environmental impact of viable tested yeasts during colic fermentation.

Colic fermentation relates to continuous fermentation with sequenced medium supplies for maintaining the flora. This medium mainly contains complex carbohydrate compounds, non-digested in the upper portion of the digestive tract (starch, pectin, cellulose . . . ), more or less hydrolyzed protide compounds and mucin.

Colic medium is also removed from the fermenter in a sequenced way. The medium is covered by a dialysis system which allows continuous removal of the soluble fermentation products.

The dialysate is collected for analyzing the short chain fatty acids (SCFA). The medium is maintained in anaerobiosis created by the specific fermentation gases and it has a redox potential of less than −300 mV. Finally, the pH is controlled with a set point value of 6.

Each digestion included: a period for stabilizing the flora of 2-3 days after sowing in the colon, a period of treatment (at least 3 days) with at least daily addition of product, and a period of stopping the treatment for 3 days.

At each experiment, the following parameters were followed and/or recorded:

the viability of the yeasts, the evolution of different aerobic and anaerobic bacterial populations, the evolution of the main fermentation products (SCFA and gases), the detection of standard enzymatic activities, and the temperature, the pH and the redox potential.

The fermentation was carried out in a penicillin flask of 60 mL, closed by a crimped septum, on 30 mL of colic medium (culture medium plus fresh fecal flora). The yeast sample was added to the 30 mL of medium.

The colic medium consisted of a microbial suspension stemming from fresh stools in a phosphate buffer on the one hand and of a typical foodstuff on the other hand, also used for cultivating colic flora in the artificial colon.

After mixing the colic medium with the product to be tested, the flask was plugged and crimped.

All these manipulations were carried out in an anaerobic hood (mixture of gases without oxygen). The flasks were placed in a rotary incubator (37° C.-200 rpm) for 24 hours.

For each product, the test was duplicated. Moreover, 4 control flasks (without any product) were prepared under the same conditions. Two flasks were treated immediately (initial time) and two flasks were incubated like the test flasks.

The fermentations were stopped after 24 hrs and the flasks were then treated.

Production of fermentative gases: The volume of gas produced by fermentation was determined by means of a Mariotte system (principle of the measurement based on the displacement of water driven out by the pressurized gas contained in the penicillin flask). Analysis of the gases present in the flask was then carried out by GPC($H_2$, $CO_2$, $CH_4$, $O_2$).

Production of short chain fatty acids: A first sampling of the colic contents was carried out. It was then either frozen, or directly treated in order to determine the SCFA concentrations (volatile short chain fatty acids) of the culture supernatant. This analysis was performed by GPC. The sought metabolites were: acetic, propionic, butyric, isobutyric, valeric, isovaleric, caproic, isocaproic and heptanoic acids.

Microbiological analysis: A second sampling of the colic contents was carried out and immediately treated (serial dilution to one tenth in a reduced dilution medium) in order to count: the total anaerobic flora, the optional aero-anaerobic flora and the fungal flora.

The results relating to the survival of the ScPro1 yeast are illustrated in FIG. 1. In this figure, each vertical arrow indicates administration of ScPro1 yeast.

It was noticed that the ScPro1 yeast shows good survival at the $3^{rd}$ day after administration and strong mortality between the $4^{th}$ and $7^{th}$ day during the administration period. This shows that this yeast is not implanted in a colic environment.

The results of the microbiological analysis are illustrated in FIG. 2. They show reduction in enterobacteria in the presence of the ScPro1 yeast with a rise after stopping administration of the yeast. During the administration of the ScPro1 yeast, it was also noticed that the flora resisting to antibiotics (chloramphenicol, genamycin) is significantly reduced.

The results relating to the effect of the ScPro1 yeast on the production of volatile short chain fatty acids (SCFA) are summarized in the table below (expressed as mM in the colic medium).

|  | Before treatment | During treatment | After treatment |
| --- | --- | --- | --- |
| Acetate | 71.4 ± 2.3 | 57.6 ± 4.2 | 60.6 ± 0.7 |
| Propionate | 22.8 ± 0.6 | 26.5 ± 4.2 | 35.7 ± 1.1 |
| Butyrate | 35.0 ± 1.6 | 36.5 ± 2.2 | 26.6 ± 4.2 |
| Isobutyrate | 3.2 ± 0.3 | 3.3 ± 0.2 | 3.4 ± 0.1 |
| Isovalerate | 5.6 ± 0.5 | 5.2 ± 0.2 | 5.3 ± 0.0 |
| Valerate | 8.0 ± 0.6 | 7.8 ± 1.4 | 9.1 ± 0.9 |
| Isocaproate | 0.1 ± 0.1 | 0.0 ± 0.0 | 0.0 ± 0.0 |
| Caproate | 9.0 ± 1.1 | 7.3 ± 0.3 | 5.7 ± 0.7 |
| Heptanoate | 0.2 ± 0.2 | 0.0 ± 0.1 | 0.0 ± 0.0 |
| Total | 155.3 ± 2.7 | 144.1 ± 6.8 | 146.4 ± 3.4 |

During treatment, a decrease of the acetate partly in favor of the propionate was noticed, which suggests a decrease in the activity of the acetogenic microflora.

Among the other monitored parameters, no acknowledged effect of the treatment was observed on Gas production (in amount and in proportion);
Concentrations of total and simple sugars (stable over time); and
Enzymatic activities.

Example 3

Study of the Influence of the ScPro1, SCB1 Yeasts on Induction of the Production of Cytokines The influence of live ScPro1 and SCB1 yeasts was studied on the induction of production of cytokines on human peripheral blood mononuclear cells (PBMC).

The ScPro1 and SCB1 yeasts were tested in their instantaneous dry form and active dry form as regards their capability of inducing production of the IL-10, ILK-12, TNFα, TNFδ cytokines in human PBMCs.

Preparation of Human Peripheral Blood Mononuclear Cells

Fresh human blood obtained from healthy subjects at the Transfusion Centre, was diluted twice with PBS-Ca (GIBCO) and purified on a Ficoll gradient (GIBCO). After centrifugation at 400×g for 30 minutes at 20° C., the peripheral blood mononuclear cells (PBMC) formed a circular layer in the serum. The PBMCs were carefully sucked up, suspended in a final volume of 50 mL using PBS-Ca and washed 3 times in the same buffer solution with 10 minute centrifugation steps at 20° C. at 350×g. The PBMCs were then re-suspended by using a complete RPMI medium (GIBCO), enriched with 10% w/v of fetal calf serum (inactivated at 56° C. for 30 minutes), 1% w/v of L-glutamine (GIBCO) and gentamycin (150 µg/mL) (GIBCO). The PBMCs were counted with a microscope, adjusted to a concentration of $2 \times 10^6$ cells/mL and distributed (in 1 mL of the aliquot solution) on 24-well cell culture dishes (Corning, Inc.).

Microbiological Preparations

Cultures produced overnight of *Lactobacillus*, *Lactococcus* and of *Escherichia coli* (control strains) were washed twice with a PBS buffer at pH 7.2, before being re-suspended in PBS at a concentration of $2 \cdot 10^9$ CFU/mL.

The yeast concentration used in the first experiments was $2 \cdot 10^8$ CFU/mL. For an initial dose comparison study, serial dilutions of 10 to 10 may be carried out in order to compare the effects of $2 \cdot 10^7$ CFU/mL, $2 \cdot 10^8$ CFU/mL and $2 \cdot 10^9$ CFU/mL.

Incubation of human peripheral blood mononuclear cells 10 µL of these working suspensions were transferred into the wells of the dishes containing the PBMCs, which were set to incubate at 37° C. in a gas mixture consisting of 5% of $CO_2$ and 95% of atmospheric air. After 24 hours of incubation, the supernatant was sucked up, centrifuged at 2,000 rpm (Eppendorf model), removed and kept at −20° C.

The control consists of Gram-positive bacteria (*Lactobacillus* and *Lactococcus*), a Gram-negative bacterium (*Escherichia coli*) and a buffer without any yeast.

Quantification of the Cytokines

The expression levels of cytokines were determined by ELISA. The ELISA plates were covered with an antibody (for one night) and the antibody was saturated with PBS/1% BSA (bovine serum albumin). A calibration was prepared with known concentrations of cytokines, with a detection threshold from 15.62 to 2,000 pg/mL (overnight incubation). The search for and quantification of anti-cytokine were carried out by measuring the streptavidin activity with the TMB substrate (tetramethylbenzidine, Pharmingen2). The commercial Pharmingen kits were used in a accordance with the description from the manufacturer. Four cytokines were selected: 3 pro-inflammatory cytokines (TNFα, INFγ, IL-12) and one anti-inflammatory cytokine (IL-10).

Results

The responses of the 4 cytokines on 5 distinct donors were evaluated at the ratio of 1/1, yeasts/PBMC.

The results of the dosages of the 4 secreted cytokines in the culture supernatant are summarized in the Table A below. The data are expressed as the average value (Avg) from the dosages of the 5 donors. The table also gives the value (Sem) of the standard error of the mean.

TABLE A

|  | IL-10 (pg/mL) | | INFγ (pg/mL) | | TNFα, (pg/mL) | | IL-12 (pg/mL) | |
|---|---|---|---|---|---|---|---|---|
|  | Avg | Sem | Avg | Sem | Avg | Sem | Avg | Sem |
| Negative control | 0 | 0 | 50 | 0 | 50 | 0 | 0 | 0 |
| E. coli | 2474 | 839 | 57376 | 29591 | 11185 | 3875 | 15 | 15 |
| Lactococcus lactis | 111 | 43 | 136103 | 62706 | 25362 | 9818 | 1101 | 543 |
| Bifidobacterium longum | 1072 | 355 | 33780 | 27164 | 14517 | 5601 | 22 | 20 |
| Lactobacillus acidophilus | 435 | 259 | 85543 | 46838 | 18369 | 6857 | 539 | 343 |
| SCB1 | 569 | 291 | 27807 | 19231 | 6492 | 2698 | 14 | 10 |
| ScPro1 | 442 | 292 | 15218 | 9304 | 3643 | 1847 | 8 | 5 |

1) For the yeasts ScPro1 and SCB1, the production of very small amounts or even undetectable amounts of IL-12 induced by the PBMCs, was observed, unlike the reference bacteria.

2) Substantial levels of IL-10 were observed both for live yeasts suggesting the SCB1 has a better result than ScPro1.

3) As regards INFγ and TNFα, the amounts secreted under the action of the ScPro1 and SCB1 yeasts are clearly smaller comparatively with the different tested probiotic bacteria.

Conclusions:

It is clearly apparent that the ScPro1 and SCB1 yeasts in the presence of PBMCs do not induce the pro-inflammatory cytokine IL-12, unlike what is traditionally observed with probiotic lactobacilli.

The ScPro1 and SCB1 yeasts in the presence of PBMCs induce substantial levels of IL-10 (anti-inflammatory).

The secreted amounts of IFN-γ and of TNF-α by the PBMCs in the presence of the ScPro1 and SCB1 yeasts are clearly smaller than with probiotic bacteria.

Example 4

Evaluation of the Protective Effect of ScPro1 and SCB1 Yeasts Towards Colitis on a Murine Chem-Induced Model (TNBS)

The proposed animal model is currently used and was adapted in order to measure anti-inflammatory effects of the yeasts.

6-week old Balb/c mice were used during this test. The mice were acclimatized to the laboratory conditions one week before the experiment, with water and food provided ad libitum. Each sample was tested on a group of 10 mice. Colitises were induced by a cycle for distributing drinking water ad libitum containing 5% (w/v-1) of TNBS for 7 days. The yeasts were orally administered by forced-feeding once a day, 3 days before the beginning of the induction of colitis by TNBS and for the duration of the TNBS treatment (7 days).

In addition to the two tested groups, the control group (negative control) was resorted to, for which only a physiological saline solution was used.

The tested parameters are the following after the treatments:

Macroscopic evaluation of the intestinal inflammation (Wallace Score). The colon of each mouse was examined under a microscope with dissection (magnification, ×5) in order to evaluate the macroscopic lesions according to the Wallace score system which ranges from 0-10 depending on evaluation criteria revealing the severity of the inflammation such as hyperemia, the thickness of the colon walls and the extent of the ulcerations.

Histological evaluation of the inflammation (Ameho Score). A section of the colon exactly sampled at 2 cm from the anal channel was used for carrying out histological evaluation according to the Ameho score which ranges from 0-6 depending on the infiltration degree of the inflammation, on the presence of erosion, ulcerations or necroses and on the depth as well as on the surface extension of the lesions. Quantification of the degradations and intestinal lesions was carried out by 2 independent operators.

Quantification of the expression of the gene coding for IL-10 and PPARα. To do this, the total RNA was isolated from the colon tissues by means of the RNeasy kit (Macherey Nagel, Hoerdt, France) according to the instructions of the manufacturer. Quantification of messenger RNA was carried out by using a spectrophotometer. After treatment at 37° C. for 30 minutes with 20-50 units of RNase-free DNase I (Roche Diagnostics Corporation, Indianapolis, Ind., USA), oligo-DT primers (Roche Diagnostics Corporation, Indianapolis, Ind., USA) were used for synthesizing the circular single strand DNAs. The messenger RNAs were quantified with the SYBR green Master Mix (Applera, Courtaboeuf, France) and with specific human oligonucleotides for studies in vitro (see Table B below), by means of the apparatus Gene-Amp Abiprism 700 (Applera, Courtaboeuf, France). Calibrated and non-calibrated controls were included in each test. Each sample was measured three times. The color intensity of the green SYBR was analyzed with the software package Abiprism 7000 SDS (Applera, Courtaboeuf, France). All the results will be normalized relatively to the gene coding for O-actin.

TABLE B

| Genes | Nucleotide primer sequences |
|---|---|
| β-actin | F: 5'-AAgTCCCTCACCCTCCCAAAAg-3'<br>R: 5'-AAgCAATgCTgTCACCTTCCC-3' |

TABLE B-continued

| Genes | Nucleotide primer sequences |
|---|---|
| PPARα | F: 5'-ACgATgCTgTCCTCCTTgATg-3'<br>R: 5'-gTgTgATAAAgCCATTGCCgT-3' |
| IL-10 | F: 5'-CAgTCAgCCAgACCCACAT-3'<br>R: 5'-gCTCCACTgCCTTgCTTT-3' |

The ScPro1 and SCB1 yeasts were tested in the standard preventive model described above. Weight monitoring of the animals before inducing the colitis showed that the preparations of yeasts administered to the mice were very well tolerated.

The intestinal inflammation, estimated by the Wallace score, was reduced by 60% with the ScProl yeast (active dry yeast, 1 mg/day) and SCB1 yeast as compared with the positive control. The SCB1 yeast also induced reduction of the inflammation. Also, intestinal necrosis estimated by the Ameho score was reduced by one third with the ScPro1 yeast (instantaneous dry yeast, 1 mg or 100 µg/day) as compared with the positive control.

The ScPro1 and SCB1 yeasts, administered alone or together, increase the level of expression of the gene coding for the anti-inflammatory interleukin IL-10 and the nuclear receptor PPARα.

FIGS. 7-10 well illustrate the excellent macroscopic Wallace and Ameho score values of the ScPro1 and SCB1 yeasts at different daily dosages.

The macroscopic Wallace score and the histological Ameho score of the ScProl1 and SCB1 yeasts in instantaneous dry form, with a daily dosage of 10 µg and 1 mg, were illustrated in FIGS. 7 and 8 respectively.

The figures of each column of the graph of FIGS. 7 and 8 represent the following elements:
1 represents TNBS alone,
2 represents TNBS+ScPro1 (1 mg),
3 represents TNBS+ScPro1 (100 µg),
4 represents TNBS+SCB1 (1 mg),
5 represents TNBS+SCB1 (100 µg).

It may be noted that the instantaneous dry ScPro1 yeast, dosed at 100 µg/day, significantly reduces the lesions at macroscopic and histological levels.

The macroscopic Wallace score and the histological Ameho score of the ScPro1 and SCB1 yeasts, taken alone or as a combination, in an instantaneous dry or active dry form, with a daily dose of 100 µg and 1 mg, are illustrated in FIGS. 9 and 10 respectively.

FIGS. 14 and 15 respectively show the expression level of the genes coding for the anti-inflammatory interleukin, and for the PPARα nuclear receptor at the intestinal cells.

The figures of each column of the graph of FIGS. 9, 10, 14 and 15 represent the following elements:
1 represents TNBS alone,
2 represents TNBS+instantaneous dry ScPro1 (100 µg),
3 represents TNBS+active dry ScPro1 (10 µg),
4 represents TNBS+active dry SCB1 (100 µg),
5 represents TNBS+active dry ScPro1 (1 µg),
6 represents TNBS+active dry ScPro1 (100 µg),
7 represents TNBS+active dry ScPro1 (100 µg)+SCB1 (100 µg).

Conclusions:

It may be noted that ScPro1 in an active dry form significantly induces lesions at a macroscopic level, and that a synergistic anti-inflammatory effect exists by the combination of ScPro1 and SCB1, both on a macroscopic and a histological level.

ScPro1 and SCB1 have respectively increased by 2.9 and 3.1 the expression level of the gene coding for the anti-inflammatory interleukin IL-10 at doses of 100 µg. The combination ScPro1+SCB1 (histogram No. 7) multiplies by 2.7 this expression level (FIG. 14).

ScPro1 and SCB1 have respectively increased by 1.5 and 1.6 the expression level of the gene coding for the PPARα nuclear receptor at doses of 100 µg. The combination ScPro1+SCB1 (histogram No. 7) multiplies by 1.7 this expression level (FIG. 15).

Example 5

Study of the Influence of the ScPro1 and SCB1 Yeasts on the Colonization of *Candida albicans* at the Intestine in a Chemo-Induced Inflammation Murine Model The study aims at determining the effects of the administration of ScPro1 and SCB1 yeasts of the probiotic type on the intestinal colonization of the pathogenic yeast *Candida albicans* and its potentialization effect of the inflammation in a chemo-induced colitis murine model.

The tested yeasts are in an instantaneous dry form.

Experimental Conditions:

The female mice of the Balb/C strain are of 4-6 weeks of age. From day 0 to day 14, the animal received DSS (Dextran Sodium Sulfate) at 1.5% in drinking water, for chemo-induction of the inflammation.

Three experiments were conducted.

In the first experiment, on day 5, the mice were forced-fed by cannula with $5 \cdot 10°$ ScPro1 yeast cells in 200 µL of PVS (phosphate buffer). This operation was renewed every day for 19 days. On day 0, the mice were forced-fed by cannula with $5 \times 10^7$ yeast cells of the *C. albicans* SC5314 strain in 200 µL of PBS.

In the second experiment, on day 0, the mice were forced-fed by cannula with $5 \cdot 10^7$ yeast cells of the *C. albicans* SC5314 strain in 200 µL of PBS. 4 days later, a batch of mice was subject to forced-feeding with $5 \cdot 10^7$ ScPro1 yeast cells in 200 µL of PBS. This operation was renewed every day for 14 days.

In the third experiment on day 0, the mice were forced-fed by cannula with $5 \cdot 10^{17}$ yeast cells of the *C. albicans* SC5314 strain in 200 µL of PBS. One hour later, a batch of mice was subject to forced-feeding with $5 \cdot 10^7$ ScPro1 yeast cells in 200 µL of PBS. This last operation was renewed every day for 14 days.

The animals (from the experiments 1, 2 and 3) were daily monitored as regards the following points:
- consistency of the stools, anal bleeding, their body mass (clinical score),
- retrocultures of 1 g of homogenized stools in 1 mL of PBS, 10 µL of each were sown on a Candi-select medium; after 24 hours of culture at 37° C., the CFUs of *C. albicans* (colored in blue) and of *S. cerevisiae* (colored in green) were counted,
- the animal were sacrificed at the end of the tests. Blood was immediately sampled by cardiac puncture, decanted at room temperature, the serum was recovered by centrifugation and stored at −80° C.; the colon was sampled and distributed in the 4 sections, 3 of them were deep-frozen and one was placed in the fixer (4% PFA) for histological study.

Results:

As this may be seen in FIG. 3, in the first experiment (prophylactic effect test), it was observed that in this model of chemo-induced colitis, administration of DSS significantly increases the colonization of the intestinal mucosas by *C. albicans* from day 4 (DSS+Ca). Very interestingly, it is seen that administration of the ScPro1 probiotic yeast for 19 days significantly reduces the colonization of *C. albicans* induced by DSS.

As shown in FIG. 4, in the second experiment (treatment test), it is observed that administration of the ScPro1 or SCB1 probiotic yeast reduces the colonization induced by DSS. Further, the effects of the ScPro1 yeast are visible even after stopping the treatment with DSS at day 14.

Conclusion:

It emerges that administration of the ScPro1 yeast or of the SCP1 yeast significantly reduces colonization of *C. albicans*, and this both under prophylactic conditions and under treatment conditions. It should be noted that this protective effect lasts even upon stopping the treatment.

Example 6

Study of the Inhibitory Effect of ScPro1 or SCB1 Yeast or Derivatives on the Adhesivity and Invasion Power of *E. Coli* Pathogenic Strains Isolated from Ileal Biopsies of Patients Affected with Crohn's Disease The influence of the live yeasts, ScPro1, SCB1 and derivatives was studied for its inhibitory effects on the adhesivity and invasive power of *E. coli* pathogenic strains isolated from ileal biopsies of patients affected with Crohn's disease.

*E. coli* strains designated as AIEC for Adherent-Invasive *E. coli* isolated from ileal biopsies of patients affected with Crohn's disease (CD) are capable of adhering and invading intestinal epithelial cells.

The LF82 *E. coli* strain, isolated from a chronic ileal lesion in a patient affected with Crohn's disease, has all the characteristics of an invasive bacterial pathogen. The characterization of an adhesion-invasion phenotype of the LF82 strain and the absence of invasion genetic determinants already described in *E. coli*, *Shigella* and *Salmonella* has lead to defining the existence of a new pathogenic group of *E. coli* which may be associated with Crohn's disease, designated as AIEC. After phagocytosis by murine or human macrophages, the AIEC LF82 strain survives and multiplies in a wide vacuole, while preserving the integrity of the host cell. Following the infection, the macrophages secrete a significant rate of TNFα. The prevalence of AIEC strains is 36.4% at ileal lesions of patients affected with CD.

The adhesion process of a bacterium to eukaryotic cells results from specific interaction between a ligand present at the surface of the bacterium, called adhesin, and a receptor of a protein, glycoprotein or glycolipid nature expressed at the surface of the epithelial cell of the host. As regards bacteria, it was shown that the FimH adhesin of pili of type I is involved in the adhesion of AIEC bacteria to intestinal epithelial cells. The bacterial FimH adhesin recognizes the CEACAM6 enterocyte receptor (also designated as CD66c or NCA) which is a glycoprotein rich in mannose residues and abnormally overexpressed at the ileal level in 90% of patients affected with CD.

Experimental Conditions:

The strain AIEC LF82 characterized for its adhesivity and invasive power of cultivated intestinal epithelial cells was used as a prototype strain.

This study was extended to 10 AIEC strains isolated from patients affected with CD in order to confirm the results obtained with the AIEC LF82 strain.

The DAEC (Diffuse Adherent *Escherichia cob*) C1845 *E. coli* strain, which adheres to epithelial cells via a mechanism independent of mannose (Afa/Dr adhesins) is used as a negative control.

Agglutination Tests

With live ScPro1 and SCB1 yeasts, quantitative agglutination tests were carried out either in the presence of AIEC bacteria, or in the presence of purified extracts of pili of type I prepared from the AIEC LF82 strain according to the procedure described in Boudeau et al. (2001 Mol. Microbiol. 39: 1272-84). An agglutination index was determined with a set yeast concentration and variable concentrations of bacteria or purified pili of type I.

In the case of yeast fractions of the mannoprotein type for which no agglutination is observed, determination of the binding capacity of pili of type I was performed by an ELISA technique.

These tests are usually conducted in microplates. The yeast fractions are fixed on a microplate. Various dilutions of purified pili of type I are put into contact with the yeast fractions. After washings, the pili of type I are revealed with anti-pili antibodies of type I obtained in rabbits (Boudeau et al., 2001). After washings, secondary antibodies coupled with peroxidase are used. Quantification is achieved with the substrate of peroxidase ($H_2O_2$) and of a chromogenic agent (tetramethylbenzidine) and by reading the microplate at the optical density of 450 nanometers.

Tests for Inhibiting the Interaction of AIEC Bacteria with the CEACAM6 Receptor Expressed at the Surface of Intestinal Epithelial Cells by the ScPro1 or SCB1 Yeast Cells used:

For the in vitro inhibition tests (pre- and co-incubation), non-differentiated T84 intestinal epithelial cells, strongly expressing the receptor CEACAM6, were retained. The T84 cells were cultivated under 5% of $CO_2$ at 37° C. in DMEM (Dulbecco's Modified Eagle's Medium) basic medium added with 50% of Ham-F12 (Life Technology) and with 10% of fetal calf serum decomplemented by heat. To this medium, were added 1% of non-essential amino acids (Life Technology), 1% of glutamine (Life Technology), 200 U/L of penicillin, 50 mg/L of streptomycin, 0.25 mg/L of amphotericin B and 1% of the X-100 vitamin mixture for MEM (Minimum Essential Medium) medium (Life Technology). The cells were sown with $4 \cdot 10^5$ cells per well and per mL and were incubated for 48 hrs at 37° C., under 5% $CO_2$. The carpet of T84 cells was then washed with PBS, and then 1 mL of the infection medium (DMEM/F12+10% of FCS) was added in each well. From an overnight culture of the AIEC LF82 strain at 37° C. in Luria-Bertani broth (LB), a bacterial suspension with an $OD_{620}$ of 0.1 in PBS was prepared. The T84 cells were infected to an infection multiplicity (MOI) of 10 bacteria for 1 cell by adding 25 μL of bacterial suspension at $OD_{620}$ of 0.1 in the infection medium. A 24-well plate was incubated for 3 hrs at 37° C. under an atmosphere enriched in $CO_2$. The adhesion and residual invasion of bacteria are achieved as described hereafter.

An experiment resorting to CHO-K1 cells which do not express CEACAM6 and these same genetically modified cells which stably express CEACAM6 (CHO-K1/CEACAM6) was used. The CHO-K1 cells were cultivated in DMEM/F12 medium, 5% of fetal calf cell serum, 1% of L-glutamine, 200 U/L of penicillin, 50 mg/L of streptomycin and 0.25 mg/L of amphotericin B. The CHO-K1/CEACAM6 cells were cultivated in DMEM/F12 medium, 5% of fetal calf serum, 1% of L-glutamine and 600 μg/mL of hygromycin. The cells were sown in a 24-well plate with $2 \cdot 10^5$ cells/well. After 7-8 hrs of incubation at 37° C., the medium is replaced with new culture medium, added with 5 mM of sodium butyrate, in order to induce the expression of CEACAM6. A Western blot was performed in order to monitor the expression of the CEACAM6 protein by the transfected cells.

After 20-24 hrs of incubation at 37° C., the cells were incubated with increasing concentrations of the instantaneous dry ScPro1 yeast strain for 1 h (pre-incubation experiment), and then they were infected with an MOI of 20 ($4 \cdot 10^6$ bacteria/well), in order to observe the bacteria/yeasts ratio used previously during experiments conducted on T84 cells. After 3 hrs of incubation at 37° C., the adhering bacteria were counted in the absence or in the presence of yeasts as described below.

Another experiment used operating parts from ill patients. The enterocytes, from ileal biopsies of 3 patients affected with Crohn's disease, were washed in PBS and then pre-incubated in an Oppendorf tube of 2 mL, in 1 mL of DMEM medium, 20% of fetal calf serum, in the presence of 0, 1.25, 2.5 or 5 mg/mL of instantaneous dry ScProl yeast strain. The tube was placed under stirring by rotation for 15 min at 37° C., and the enterocytes were then infected, in the presence of the yeasts, with 50 µL of an overnight LB culture of the AIEC LF82 strain. An incubation of 3 hrs with stirring was performed. The enterocytes were washed twice in PBS, and then deposited between slide and lamella and observed in phase contrast microscopy. Countings of bacteria adhering to the brush border of the enterocytes were carried out in the presence or in the absence of yeasts. The experiment was also conducted with the non-piliated mutant LF82-delta fimH, in order to determine the basal adhesion level of AIEC bacteria not bringing into play the recognition of the pili of type I at the CEACAM6 receptors. Also, adhesion inhibition experiments were conducted in the presence of anti-CEACAM6 antibodies.

Procedure followed for measuring the adhesion and residual invasion of bacteria to intestinal epithelial cells T84

The cell carpet was washed 4 times with 1 mL of PBS and the cells were then lyzed by 5 min of incubation at room temperature with 500 µL of 1% Triton X-100 in distilled water. The lyzates were diluted and then spread out on LB-Agar gelose in order to determine the number of CFUs, corresponding to the number of adhering bacteria.

In order to count the invasive bacteria, the cell carpet was washed with PBS following the 3 hrs of infection, and was then incubated for 1 h with 1 mL of infection medium containing 100 µg/mL of gentamycin, in order to destroy the extracellular bacteria. The invasive bacteria were counted after lysis of the cells, serial dilutions and spreading-out on LB-Agar gelose.

The adhesion and invasion levels of the AIEC LF82 strain were analyzed comparatively to cells infected by the AIEC LF82 strain not having been subject to any treatment by yeasts or yeast derivatives.

All the results are expressed according to the ratio R:

R=Number of adherent or invasive bacteria in the presence of the ScPro1 yeast/Number of adherent or invasive bacteria without any treatment.

Procedure 1: Co-incubation model

The T84 cells and the bacterial suspension were prepared as described above, during adhesion and invasion tests. The yeasts or the derivatives of yeasts were suspended in PBS at a determined concentration, and then 25 µL of this suspension were added into the infection medium of T84 cells (1 mL). The cells were then immediately infected at MOI=10 with the bacterial strain. The suspension of bacteria/incubated yeasts in the presence of cells was homogenized, and the 24-well plate was incubated for 3 hrs at 37° C. The adhesion and invasion levels of the bacterial strain were determined as described above, and this, in the absence and in the presence of yeasts or yeast extracts during the infection. The ratio between the bacterial adhesion or invasion level in the absence of yeast (100%) and the bacterial adhesion or invasion level in the presence of yeasts represents the residual adhesion and invasion level of the bacteria.

Procedure 2: Pre-Incubation Model

The T84 cells and the bacterial suspension were prepared as described above, during adhesion and invasion tests. The suspension of yeasts or yeast derivatives was added into the infection medium (1 mL) of the T84 cells in a volume of 25 µL. The yeast suspension was homogenized and the 24-well plate of cells was incubated for 1 h at 37° C. Following this incubation, the T84 cells were infected by the bacterial strain, at MOI=10, in the presence of yeasts, and this at 3 hrs at 37° C. Counting of the adherent and invasive bacteria was carried as described above, in the presence or in the absence of yeasts, in order to determine a residual adhesion or invasion percentage, where 100% represents the adhesion or invasion in the absence of yeast.

Verification of the expression of CEACAM6

Immunocytochemical labelings were carried out on each batch of cultivated cells in order to verify the presence and estimate the expressed amount of CEACAM6. The cells were cultivated on sterile glass lamellas. The cell carpet was washed with PBS, and then fixed by 3% paraformaldehyde at pH 7.4 for 10 minutes at room temperature. The cells were incubated with the anti-CECAM6 monoclonal antibody (clone 9A7, Genovac) diluted to 1/100 in PBS-5% horse serum, in a humid atmosphere for one hour. After washing with PBS, the cells were put into contact with a secondary antibody coupled to a fluorochrome (FITC-anti-mouse, Zymed) diluted to 1/500 in PBS-5% horse serum, for 1 hour in a humid atmosphere. The glass lamellas were fixed on the slide with Moewiol, and then viewed with a fluorescence microscope.

Checking the absence of cell cytotoxicity

The absence of cell cytotoxicity induced by the different doses of yeast was tested by dosing lactate deshydrogenase (LDH) in the yeasts/cells or FDL/cells incubation medium (Glasser et al., 2001).

Results:

Agglutination Tests with LF82

The agglutination titers obtained with LF82 in the presence of the cultivated ScPro1 or SCB1 yeast (=fresh form) or in a dry form (instantaneous or freeze-dried dry form) are summarized in the following table which is the result of 3-5 independent experiments:

| Yeast | - Form | Agglutination titer | | |
|---|---|---|---|---|
| | | Average | Mean. titer | Max. titer |
| ScPro1 | Fresh culture | 1/7 | 1/3 | 1/12 |
| ScPro1 | Instantaneous dry | 1/58 | 1/20 | 1/96 |
| ScPro1 | Freeze-dried dry | 1/43 | 1/24 | 1/64 |
| SCB1 | Fresh culture | 1/28 | 1/12 | 1/40 |
| SCB1 | Instantaneous dry | 1/16 | 1/12 | 1/20 |
| SCB1 | Freeze-dried dry | 1/19 | 1/16 | 1/24 |

Absolutely, good agglutination results with LF82 are obtained with dry yeast, instantaneous dry ScPro1 and instantaneous dry SCB1.

For these yeasts, the significance of the favorable impact of the method and notably of the drying method on its agglutination potential was shown.

Agglutination Tests with Purified Pili

The agglutination titers obtained with purified pili in the presence of the cultivated ScPro1 yeast (=fresh form) or in the instantaneous dry form and of the (dry) SCB1 yeast are summarized in the following table:

| Yeast | Form | Agglutination titer | | |
|---|---|---|---|---|
| | | exp 1 | exp 2 | exp 3 |
| ScPro1 | Pressed fresh yeast | 1/300 | 1/300 | 1/400 |
| ScPro1 | Instantaneous dry | 1/600 | 1/600 | 1/300 |
| SCB1 | Freeze-dried dry | 1/300 | 1/300 | 1/200 |

This experiment confirms that a pili-yeast interaction is actually required for agglutination. As the pili have the property of recognizing mannose structures, the latter are the ones which are recognized on yeasts and which are involved in the observed agglutination phenomenon. The best results are obtained with instantaneous dry ScPro1 yeast.

Result of the test for determining the binding capacity of pili of type 1 on mannoprotein fractions of ScPro1 yeast FIG. 18 clearly shows that the purified pili of type 1 from the strain AIEC LF82 specifically bind to the yeast mannoproteins. It is noted that the preparation method (thermal or enzymatic method) of these mannoproteins (EL05 and EL06) has a slight influence on the affinity constant of the pili.

Results of inhibition of the interaction of AIEC bacteria with the CEACAM6 receptor expressed at the surface of epithelial cells 1/ Results of the Screening of Samples of Yeasts or Yeast Derivatives for their Power of Inhibiting Adhesion and Invasion of the AIEC LF82 Strain to T84 Intestinal Epithelial Cells in a Co-Incubation Model.

The instantaneous dry ScPro1 yeasts ($3.09 \cdot 10^7$ yeasts/mg), dry ScPro1 yeast ($1.86 \cdot 10^7$ yeasts/mg) and instantaneous dry ScB1 yeast ($5.83 \cdot 10^\circ$ yeasts/mg), as well as the mannoproteins of EL05 yeast (dry form) were investigated.

As a comparison, Ultra-levure® (Biocodex with $2.054 \cdot 10^\circ$ yeasts/mg) was added.

Comparison of the Inhibitory Power of Yeasts with Identical Numbers of Yeasts in the Co-Incubation Model.

After washing in PBS and 15 min centrifugation at 7,500 rpm, the yeast samples were resuspended at a concentration of $4 \cdot 10^8$ yeasts/mL in PBS. Dilutions of the yeasts in PBS were carried out: ½, $1/10^{th}$, $1/20^{th}$, and $1/100^{th}$.

Thee independent experiments were conducted by using the procedure 1. The results in FIGS. 19A and 19B (residual adhesion and residual invasion) are shown as means of the residual adhesion and invasion rates and the error bars correspond to the standard error of the mean.

Figure 19A:
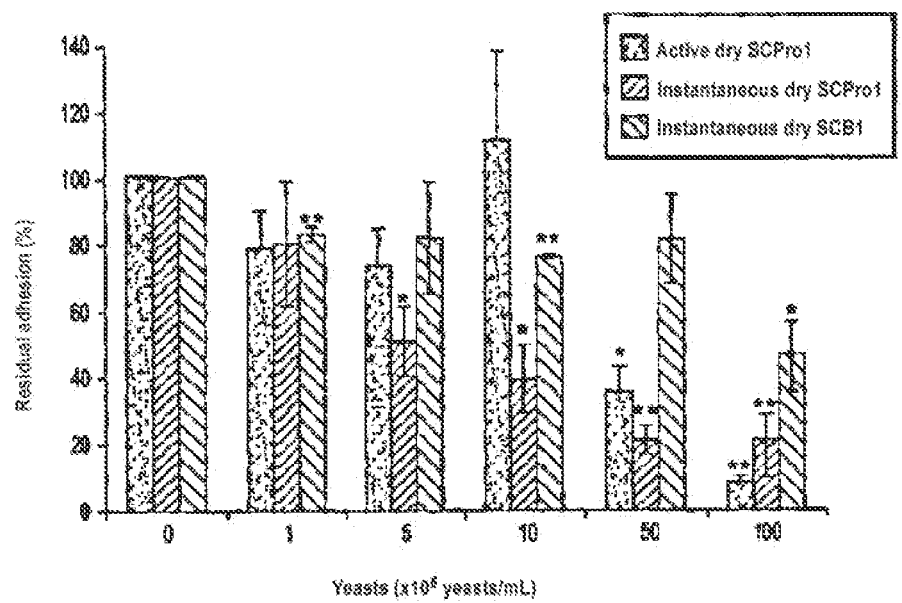
Figure 19B:
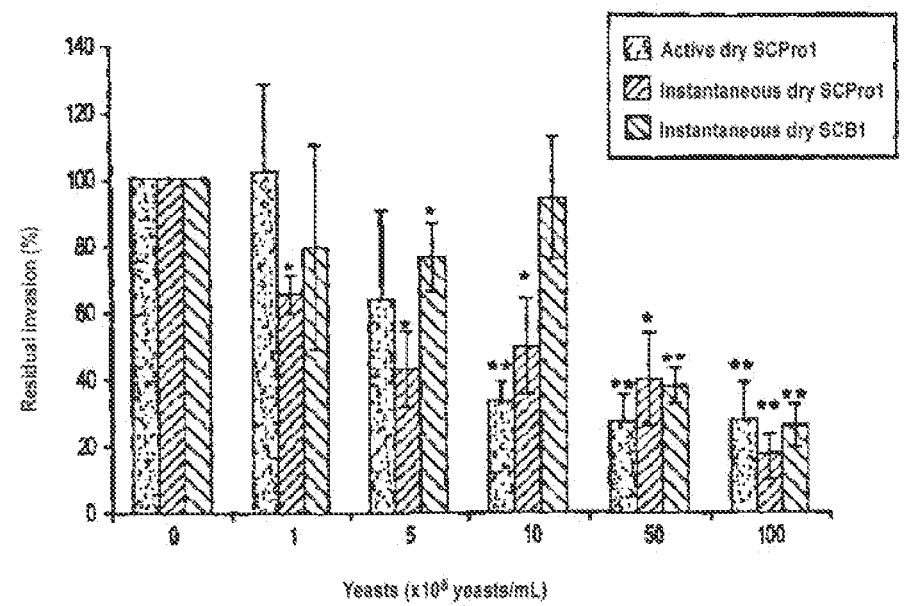
Figure 20A:
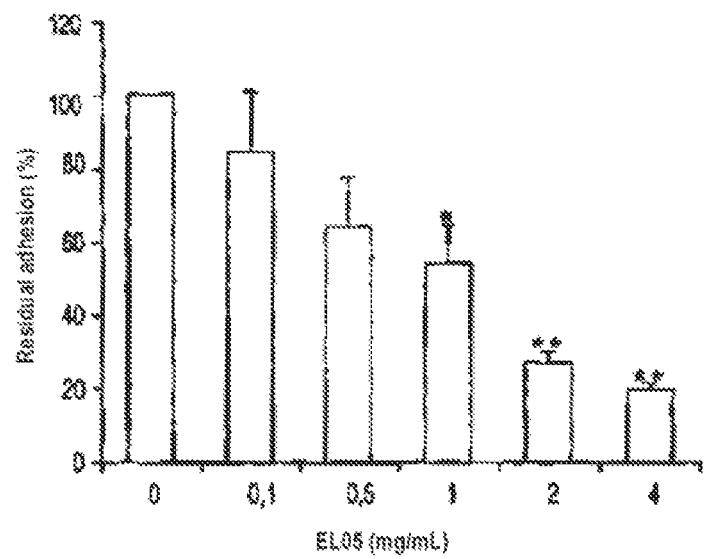
Figure 20B:
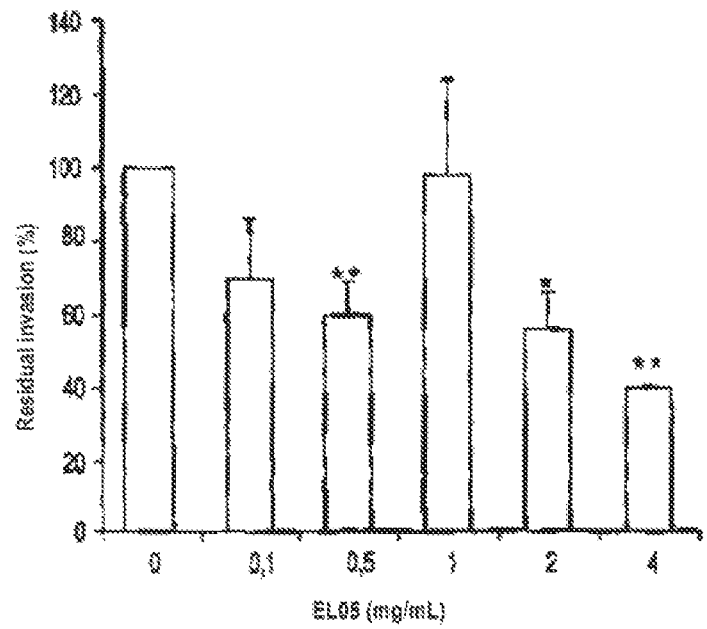

FIGS. 19A and 19B allow the following results to be obtained:

Adhesion:
The instantaneous dry ScPro1 and dry ScPro1 yeasts strongly inhibit the adhesion of the strain LF82 to T84 cells in a dose-dependent way. Inhibition is significant from $5 \cdot 10^5$ yeasts/mL for the instantaneous dry ScPro1 yeast, versus $5 \cdot 10^6$ yeasts/mL for the dry ScPro1 yeast.

The instantaneous dry ScB1 yeast less strongly inhibits adhesion than the 2 other yeast samples with 45.7% of residual adhesion at $1 \cdot 10^7$ yeasts/mL, versus 18.7% and 8% of residual adhesion for the instantaneous dry ScPro1 and dry ScPro1 strains, respectively.

Invasion:
The instantaneous dry ScPro1 yeast significantly inhibits the invasion of T84 cells by the AIEC LF82 strain from $1 \cdot 10^5$ yeasts/mL. At $1 \cdot 10^7$ yeasts/mL, the residual invasion rate is 16.3%.

For the dry ScPro1 and instantaneous dry ScB1 yeasts, the inhibitory effect is more belated, from $1 \cdot 10^6$ yeasts/mL and $5 \cdot 10^6$ yeasts/mL, respectively.

Inhibition Tests with EL05 Mannoproteins in the Co-Incubation Model

EL05 yeast mannoproteins were suspended in PBS at a concentration of 160 mg/mL. Serial dilutions were carried out in PBS: ½, ¼ ⅛, $1/40$ and 25 μL of each suspension of mannoproteins were added to the infection medium while using procedure 1.

Three independent experiments were conducted. The results illustrated by FIGS. 20A and 20B (Residual adhesion and residual invasion) are shown as means of the residual adhesion rates and the error bars correspond to the standard error of the mean.

These figures show that the EL05 yeast mannoproteins have the capability of inhibiting adhesion and invasion of the AIEC LF82 strain to T84 cells in a dose-dependent way in the co-incubation model.

2/ Screening of Samples of Yeasts or Yeast Products for their Power of Inhibiting Adhesion and Invasion of the AIEC LF82 Strain to T84 Intestinal Epithelial Cells in a Pre-Incubation Model.

The same samples of yeast and fractions as those which were used for the co-incubation model were used in this pre-incubation model.

Comparison of the Inhibitory Power of Yeasts with Identical Numbers of Yeasts in the Pre-Incubation Model After washing in PBS and 15 min centrifugation at 7500 rpm, the yeast samples were resuspended at a concentration of $4 \cdot 10^8$ yeasts/mL in PBS. Dilutions of the yeasts in PBS were carried out: ½ $1/10$, $1/20$ and $1/100$. Three independent experiments were conducted while using procedure 2.

Figure 21A:
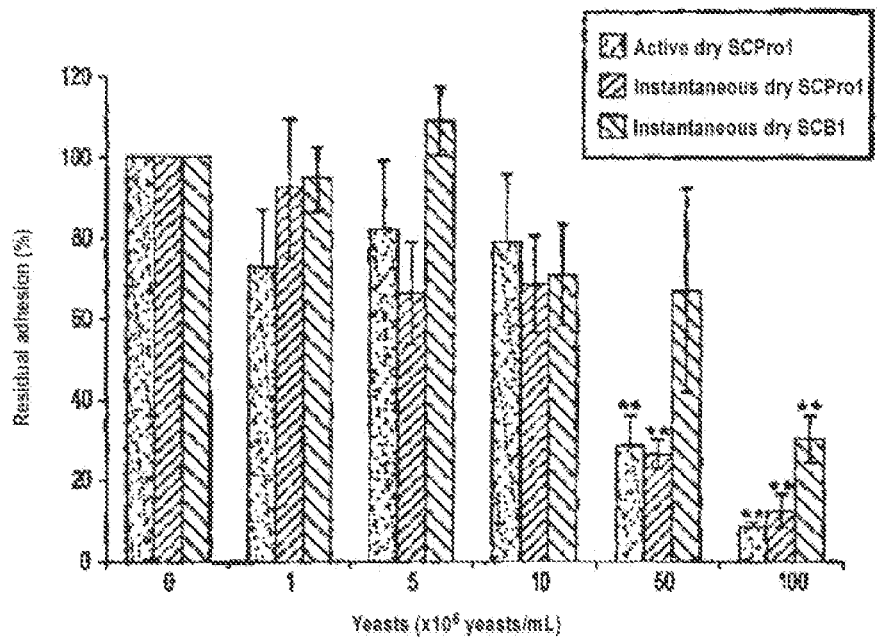
Figure 21B:
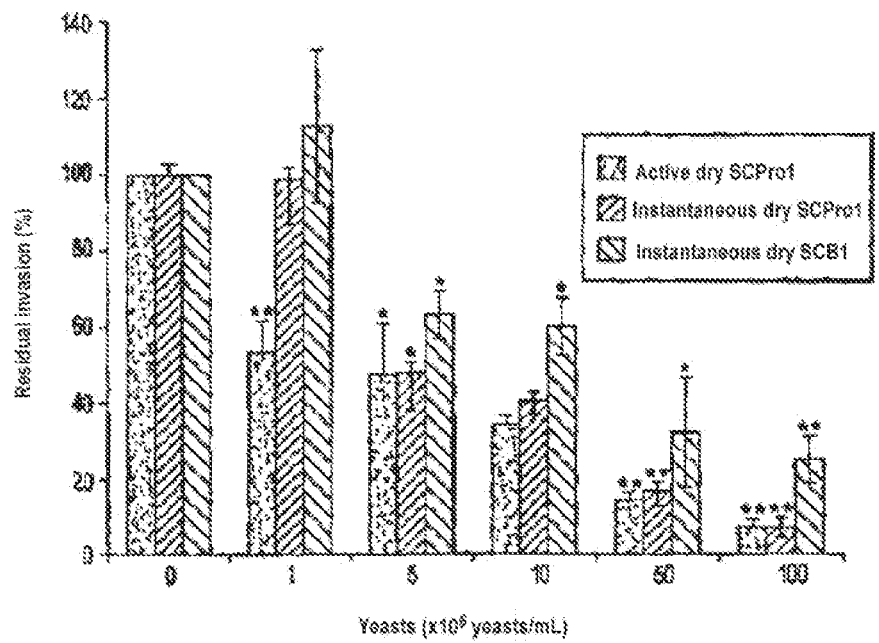

The results illustrated by FIGS. 21A and 21B (residual adhesion and residual invasion) are shown as means of the residual adhesion and invasion rates and the error bars correspond to the standard error of the mean.

By pre-treating T84 cells with yeasts, it is possible to obtain significant inhibition of the adhesion of the LF82 strain from the dose of $5 \cdot 10^6$ yeasts/mL for the instantaneous dry ScPro1 and dry ScPro1 strains. However, at this dose, no significant inhibition was observed with the instantaneous dry ScB1 yeast.

By pre-treating T84 cells with yeasts, it is possible to obtain an inhibition of the invasion of the LF82 strain from the dose of $1 \cdot 10^5$ yeasts/mL for the dry ScPro1 yeast strain.

From the dose of $5 \cdot 10^5$ yeasts/mL, the 3 yeast samples induce significant decrease in the invasion of the LF82 strain.

Inhibition Tests with EL05 Mannoproteins in the Pre-Incubation Model

Mannoproteins of EL05 yeasts were suspended in PBS at a concentration of 160 mg/mL. Serial dilutions were performed in PBS: ½ ¼, ⅛ and $1/40$ and 25 μL of each suspension of mannoproteins were added to the infection medium while using procedure 2. Three independent experiments were conducted. The results of FIGS. 22A and 22B (residual adhesion and residual invasion) are shown as means of the residual adhesion rates and the error bars correspond to the standard error of the mean.

The EL05 mannoproteins allow inhibition in a dose-dependent way of the adhesion and invasion of the LF82 strain from the concentration of 2 mg/mL.

Results of the Inhibition Test by Yeasts on the Adhesion of the AIEC LF82 Strain to CHO-K1 Cells Either Expressing the CEACAM6 Receptor in the Pre-Incubation Model or not Five independent experiments were conducted while using procedure 2 as mentioned earlier.

FIG. 23 shows significant inhibition of the adhesion of the AIEC LF82 strain, observed with CEACAM6/CHO cells from the pre-incubation with 25 pg/mL of yeasts. A dose-dependent inhibitory effect is observed with these cells.

Adhesion of the AIEC LF82 strain is also observed to CHO-K1 cells, certainly due to the expression of mannosylated proteins expressed at the surface of these cells. However, pre-incubation of the LF82 strain with the instantaneous dry ScPro1 yeast does not allow very significant inhibition of the adhesion to non-transfected cells.

This therefore confirms that the yeast interferes in the adhesion of the LF82 strain to the CEACAM6 receptors expressed by the cells.

Results of Inhibition of the Adhesion of the AIEC LF82 Strain at the Brush Border of Enterocytes of Patients Affected with Crohn's Disease in the Pre-Incubation Model.

FIG. 24 shows the mean adhesion indices obtained during the experiment and they were calculated in the presence or in the absence of increasing concentrations of instantaneous dry ScPro1 yeast (mg/mL) or in the presence of anti-CEACAM6 antibodies. According to the results of this figure, a significant and dose-dependent reduction of the AIEC LF82 strain is reported at the brush border of the enterocytes of patients when in presence of the instantaneous dry ScPro1 yeast strain. At the dose of 5 mg/mL of yeasts, the residual adhesion of the AIEC LF82 strain is similar to that observed in the presence of anti-CEACAM6 antibodies or to that observed for a mutant without any pili of type 1.

Conclusion:

From this study it emerges that:
- the ScPro1 and SCB1 yeasts, in particular in the instantaneous dry form, have strong power for agglutination of the LF82 strain.
- the ScPro1 and SCB1 yeasts are capable of inhibiting in vitro the adhesion and invasion of human epithelial cells (T84, ileal biopsy enterocytes) and of CHO cells expressing the human CEACAM6 receptor by *E. coli* in a dose-dependent way.
- the mannoproteins are capable of inhibiting in vitro the adhesion and invasion of human epithelial cells (T84, ileal biopsy enterocytes) and of CHO cells expressing the human CEACAM6 receptor by *E. coli* in a dose-dependent way.
- in vitro, the ScPro1 yeast is capable at strong concentrations, of partly protecting about 80% of the cells from bacterial infection.

Example 7

Study of the Regulatory Role of ScPro1, SCB1 Yeasts and of Yeast Derivatives on the Expression of the Genes Coding for IL-10 and PPARα in Human Intestinal Epithelial Cells Cultivated In Vitro The probioticity of ScPro1 and SCB1 yeasts was investigated, either taken alone or in combination, and/or of yeast fractions, and their capability of inhibiting the triggering of inflammations by interaction with certain intestinal receptors.

Tests In Vitro

The effects of the yeast and of the yeast derivatives according to the invention were notably studied on different receptors of intestinal epithelial cells by analysis in vitro on two colon cancer cell lines CaCo-2 (ATCC HTB-37) and HT-29 (ATCC HTB-38).

For this, transcriptional analysis was carried out by extracting the RNA, according to the following method.

The cells are lyzed in Trizol. On the soluble fraction, a deoxyribonuclease step is carried out by adding 200 µL of a solution containing 10 U of ribonuclease inhibitor and 10 U of deoxyribonuclease.

10 µg of RNA were back-transcribed in the presence of 200 U of inverse transcriptase, dithiothreitol, of oligo-dT15 and of deoxyribonucleotides.

The cDNAs are amplified by the known polymerase chain reaction technique (PCR) at the same time as a competitor by using specific sense and anti-sense primers, notably the following genes: IL-10 and PPARα.

After 40 cycles of amplification, conducted in the presence of 1.25 U of Ampli Taq Gold 5000 and migration of the different samples on a 3% agarose gel, the intensity of the bands is determined by an image analyzer.

The results are expressed in the number of mRNA molecules for $10^5$ molecules of an internal standard: β-actin.

The results, grouped in FIG. 11, comprise the mRNA expression values one after (under reference A) and 3 hours after (under reference B) putting the yeasts or derivatives in contact with the intestinal epithelial cells of the gene coding for the anti-inflammatory protein IL-10.

In this FIG. 11, the following references designate the tested yeasts/yeast derivatives which have shown an early expression level greater than 4 times the reference signal:
- 3 designates a *Saccharomyces cerevisiae* yeast,
- 5 designates the ScPro1 yeast of the invention,
- 6 designates an extract of *Saccharomyces cerevisiae* yeast, and
- 12 designates an RNA fraction of *Saccharomyces cerevisiae* yeast.

These results actually show that the yeast and the derivatives of *Saccharomyces cerevisiae* yeast, according to the invention, induce early expression, after one hour, of the gene coding for the anti-inflammatory cytokine, IL-10.

Indeed, as compared with the untreated control, the mRNA expression for the yeast and the derivatives according to the invention is greater than 4 on the axis of the ordinates, a value which already corresponds to an excellent early expression signal.

Other results are grouped in FIG. 13. This figure shows the modulation, depending on the provided amounts of yeast derivatives, of the mRNA expression of the gene coding for the IL-10 protein.

In this FIG. 13, the expression was measured after one hour (1 h) and after three hours (3 hrs). The expression of the yeasts and *Saccharomyces cerevisiae* extracts according to the invention may be seen, designated by the following references:
- 5 designates the ScPro1 yeast according to the invention,
- 6 designates a *Saccharomyces cerevisiae* yeast extract,
- 8 designates a parietal β-glucan of *Saccharomyces cerevisiae*,
- 9 designates a parietal mannoprotein of the yeast *Saccharomyces cerevisiae*,
- 11 designates a DNA fraction of the *Saccharomyces cerevisiae* yeast, and 12 designates an RNA fraction of the *Saccharomyces cerevisiae* yeast.

The expression was measured with different concentrations of yeast and/or derivative.

The darker the color of the columns in FIG. 13, the higher is the concentration if yeast/derivative.

The results of this FIG. 13 show that the *Saccharomyces cerevisiae* yeast extracts according to the invention prematurely induce the mRNAs of the anti-inflammatory cytokine (IL-10).

The results grouped in FIG. 12 comprise the mRNA expression values, one hour (under reference A), and 3 hours (under reference B), after putting the yeasts or derivatives in contact with the intestinal epithelial cells, of the gene coding for the nuclear receptor PPARα.

In this FIG. 12, the following references designate the tested yeasts/yeast derivatives, which have shown a belated expression level greater than 3 times the reference signal:

1 designates the *Saccharomyces cerevisiae* ScPro1 yeast according to the invention in active dry form, 4 designates a *Saccharomyces cerevisiae* yeast, 5 designates the *Saccharomyces cerevisiae* Scpro1 yeast according to the invention in an active dry form, 8 designates a fraction of *Saccharomyces cerevisiae* yeast walls, 9 designates a fraction of parietal β-glucans of *Saccharomyces cerevisiae* yeast, 10 designates a fraction of parietal mannoproteins of *Saccharomyces cerevisiae* yeast, 11 designates a DNA fraction of *Saccharomyces cerevisiae* yeast, and 12 designates an RNA fraction of *Saccharomyces cerevisiae* yeast.

These results actually show that the yeast and derivatives of *Saccharomyces cerevisiae* yeast, according to the invention, induce the expression in a belated way, after three hours, of the gene coding for the nuclear receptor PPARα.

Indeed, the mRNA expression for the yeast and the derivatives according to the invention is greater than 3 on the axis of the ordinates, a value which already corresponds to an excellent belated expression signal.

Example 8

Study Ex Vivo of the Regulatory Role of Yeasts and of Yeast Derivatives on the Expression of the Genes Coding for IL-10 and TNF-α in Human Intestinal Epithelial Cells Isolated from Biopsies of Patient Affected with Crohn's Disease The influence of the yeasts and/or yeast derivatives on the secretion of the cytokines, IL-10 (anti-inflammatory) and TNF-α (pro-inflammatory), was studied ex vivo on biopsies of patients either affected with Crohn's disease or not.

Intestinal biopsies were sampled on patients either affected with Crohn's disease or not, and then placed for 24 hrs in HBSS-CMF medium supplemented with penicillin and streptomycin, at 37° C. in an atmosphere containing 5% of $CO_2$. After washing, the biopsies were put into contact with the yeasts or the yeast derivative for 4 hours in RPMI 1640 medium. The supernatant was recovered for analysis by ELISA. The biopsies were then lyzed in order to allow either extraction of mRNAs or of total proteins.

Confirmation of the secretion of the cytokines was achieved by immunological analysis of supernatants of cell cultures and of the proteins extracted by ELISA. The proteins denatured for 5 minutes at 95° C. in a deposit buffer (vol/vol; 75 mM Tris pH 6.8; 5% glycerol; 0.25% bromophenol blue; 2% SDS, 5% β-mercaptoethanol were deposited (50 µg) and resolved on a 10% polyacrylamide gel. After migration, the proteins were transferred on a PVDF membrane (Hybond-P, Amersham Pharmacia Biotech, Orsay, France) by semi-dry electrotransfer (Hoefer TE77, Amersham Pharmacia Biotech, Orsay, France) for 1 hour at 16 V. PPARα and IL-10 were revealed by means of human anti-PPARα and anti-IL-10 rabbit polyclonal antisera, diluted to 1/500 and quantified by chemiluminescence (E.C.L. Amersham Pharmacia Biotech, Orsay, France) on a Biomax-MR film (Kodak) with the software package Gel Analyst (CLARA VISION, Paris, France).

FIGS. 16 and 17 show the results obtained for IL-10 and TNF-α, respectively. The axis of the ordinates indicates the amounts of cytokines measured in pg/mL. Each point corresponds to the measurement of the biopsy on a patient affected with Crohn's disease in the acute phase (black circle), on a patient in remission of Crohn's disease (grey circles) and on healthy patients (white circle). A bar indicates the mean of the measurements.

In these figures:

1 designates the *Saccharomyces cerevisiae* ScPro1 yeast according to the invention in an active dry form, 3 designates a *Saccharomyces cerevisiae* yeast, 8 designates a fraction of *Saccharomyces cerevisiae* yeast walls, 11 designates a DNA fraction of *Saccharomyces cerevisiae* yeast, and 12 designates an RNA fraction of *Saccharomyces cerevisiae* yeast.

In FIG. 16, the ScPro1 yeast according to the invention multiplies by 2 secretion of the anti-inflammatory cytokine, IL-10, by epithelial cells of patients affected with Crohn's disease or in remission as compared with healthy patients and with the negative control (−) corresponding to the measurements carried out in the presence of only physiological saline.

FIG. 17 shows that the ScPro1 yeast according to the invention does not cause any increase in the secretion of the pro-inflammatory cytokine, TNF-α, by intestinal cells isolated from biopsies of patients affected with Crohn's disease or in remission. ScPro1, or none of the other tested yeasts or yeast derivatives induced any secretion of TNF-α.

Example 9

Study of Analgesic Properties of Yeasts and of Yeast Derivatives in a Murine Model of Colorectal Distension In Healthy Rats 1/ Equipment and Methods Male Sprague Dawley rats (Charles River, l'Arbresle, France) weighing between 175 and 200 g are used during these tests. The rats are acclimatized to animal house conditions one week before the experiment. They are kept in a number of five animals per cage, with water and food ad libitum. All the tests are conducted according to the recommendations of the Committee for Research and Ethical Issues of the International Association for the Study of Pain [6]. Precautions are taken in order to avoid or minimize discomfort of the animals.

2/ Evaluation of the Sensitivity of the Colon

Nociception of the animals is estimated by measuring the intracolon pressure required for inducing a behavioral response. This pressure is generated by colorectal distension by means of the inflation of a balloon introduced into the colon. The behavioral response is characterized by a rise in the rear portion of the body of the animal and a clearly visible abdominal contraction corresponding to severe contractions [7-9]. The rats are anesthetized with a volatile anesthetic (2% isoflurane) and the balloon (prepared according to the procedure described by Bourdu [8]) is inserted via an intrarectal route in an as less invasive as possible way, at 7 cm from the anus. The catheter is attached to the base of the tail with an adhesive tape. After 5 minutes, the rats are placed in the middle of a Plexiglas box and the catheter is connected to an electronic barostat (Distender Series IIRTM, G & J Electronics). Increasing pressure is continuously applied until triggering of the pain reflex or until the limiting pressure of 80 mm of mercury is reached.

3/ Administered Compounds

The yeasts were administered by forced-feeding once a day for 15 days.

The morphine injected intraperitoneally at a dose of 1 mg/kg is used as a positive control, 30 min before the colorectal distension.

8 groups of rates were investigated:
10 control rats receiving PBS,
10 rats receiving the instantaneous dry ScPro1 (100 µg/d), reference 1)
10 rats receiving the active dry ScPro1 strain (100 µg/d), (reference 2)
10 rats receiving the SCB1 strain (100 µg/d), (reference 3)
10 rats receiving the instantaneous dry ScPro1 (50 µg/d)+ instantaneous dry SCB1 (50 µg/d) strains (reference 4)
10 rats receiving one injection of morphine (1 mg/kg, 30 min before distension) (reference 5).

4/ Results

FIG. 26 shows on the one hand that the ScPro1 yeast in its instantaneous dry form, administered alone (reference 1) or in combination with the SCB1 strain (reference 4), and in its active dry form (reference 2) on the other hand, increases the pain perception threshold, thereby significantly reducing the perception of visceral pain as compared with rats to which nothing was administered.

The following results are given in mm of mercury as a comparison with the control:
74.5±3.07 vs. 53.6±3.9, p=0.07 for the instantaneous dry ScPro1 strain—(reference 1),
66.5±3.36 vs. 53.6±3.9, p=0.04 for the combination of instantaneous dry ScPro1 and SCB1 strains—(reference 4),
72±2.59 vs. 53.6±3.9, p<0.01 for the instantaneous dry ScPro1 strain—(reference 2), On the other hand, this effect is comparable with the one induced by morphine—reference 5—used at the dose of 1 mg/kg with a pain threshold of 72±2.59 mm of mercury.

The instantaneous dry SCB1 strain also induces an analgesic effect in healthy rats, 70.6±3.10 mm of mercury p=0.026.

In rats having visceral hypersensitivity

1/ Equipment and Methods

Female Sprague Dawley rats (Charles River, L'Arbresle, France) weighing between 175 and 200 g were used. The rats were acclimatized to the laboratory conditions one week before the experiment. They were kept in a number of 5 animals per cage with water and food ad libitum. All the tests were conducted according to the recommendation of the Committee for Research and Ethical Issues of the International Association for the Study of Pain [6]. Great precautions were taken as regards the living conditions in order to avoid or minimize discomfort of the animals.

2/ Induction of Hypersensitivity of the Colon by Washings with Butyrate

For each washing, a catheter (2 mm Fogarty) was introduced into the colon at 7 cm from the anus and the animals received twice daily for 3 days, 1 mL of 200 mM sodium butyrate solution with neutral pH (pH 6.9). The "healthy" animals received a saline solution.

3/ Treatment of the Animals with the Yeasts According to the Invention 10 groups of animals having visceral hypersensitivity were used (n=10 per group). The treated animals received 100 µg of yeasts by gastric forced-feeding, once a day for 15 days. The control animals received the PBS according to the same procedure as earlier. The yeasts are suspended in a solution of PBS. The instillations of butyrate or of saline solutions begin 7 days after the first forced-feeding, for 3 days. The colic hypersensitivity was measured 14 days after the beginning of the treatment via an oral route, i.e. 7 days before the colic instillations.

4/ Groups of Studied Animals

Seven groups of rats were studied. The numerical references correspond to FIG. 26.
10 rats receiving PBS (control),
10 rats receiving instantaneous dry ScPro1 dry yeast (100 µg/d)—(reference 1),
10 rats receiving active dry ScPro1 dry yeast (100 µg/d)—(reference 2),
10 rats receiving instantaneous dry ScPro1 yeast (100 µg/d)—(reference 3),
10 rats receiving instantaneous dry ScPro1 (50 µg/d) and instantaneous dry SCB1 (50 µg/d)—(reference 4),
10 rats receiving morphine—(reference 5),
10 rats receiving fibrates—(reference 6).

5/ Results

It should first of all be noted that for the control rats, the pain threshold in the test on hypersensitized rats is below the one of healthy rats.

The instantaneous dry ScPro1 yeast, taken alone or as a combination with the SCB1 yeast, show interesting analgesic effects in the model.

The numerical values are the following:

| References | mm of mercury |
|---|---|
| 1 | 56.5 ± 4.27 p = 0.03 |
| 4 | 59 ± 4.33 p = 0.02 |

The yeasts according to the invention allow restoration of a pain perception level identical with the one observed in healthy rats. The analgesic effect induced by the yeasts is equivalent to the one induced by morphine.

FIG. 26 moreover shows a strongly analgesic effect of fenofibrate which increases by a factor 2 the pain perception threshold in rats having visceral hypersensitivity (70±4.48 p=0.001).

This result confirms the role of the PPARα receptor in the modulation of the visceral pain.

The invention claimed is:
1. A composition of yeast cells comprising:
(i) cells having all the identifying characteristics of *Saccharomyces cerevisiae* yeast strain deposited at the Collection Nationale de Cultures de Microorganismes under No. CNCM I-3856, and/or
(ii) cells having all the identifying characteristics of *Saccharomyces cerevisiae* var. *boulardii* yeast strain depos- ited at the Collection Nationale de Cultures de Microorganismes under No. CNCM I-3799, and
(iii) at least one excipient.

2. The composition according to claim 1, wherein said yeast cells of at least one of said yeast strains are is in a dry or fresh form.

3. The composition according to claim 2, wherein said yeast cells of at least one of said yeast strains are in an instantaneous dry or active dry form.

4. The composition according to claim 1, wherein the composition comprises between $10^7$ and $6 \times 10^{10}$ CFU of said yeast cells of at least one of said yeast strains.

5. The composition according to claim 1, wherein the composition comprises between 1 mg and 10 g of of said yeast cells of at least one of said yeast strains.

6. The composition according to claim 1, comprising between $10^8$ and $2 \times 10^{10}$ CFU of said yeast cells of at least one of said yeast strains.

7. The composition according to claim 1, comprising between 1 mg and 1 g of said yeast cells of at least one of said yeast strains.

8. The composition according to claim 1 further comprising at least one *Saccharomyces cerevisiae* yeast derivative selected from yeast extracts, wall derivatives, parietal glucans, parietal mannoproteins, lipid yeast fractions, and yeast nucleic acid (RNA, DNA) fractions.

9. A method for increasing resistance to pain or for reducing pain in a subject comprising a step of administering to said subject an effective amount of a composition according to claim 1.

10. The method according to claim 9, wherein the pain results from hyperalgesia.

11. The method according to claim 9, wherein the pain is selected from intestinal pains, chronic visceral pains, and pains resulting from hyperalgesia associated with bowel pathologies and disorders.

12. The method according to claim 9, wherein the pain is associated with a disease or disorder selected from functional intestinal disorders, functional intestinal pain syndrome, chronic inflammatory bowel diseases, food intolerances, irritable bowel syndrome, ulcerative colitis, hemorrhagic rectocolitis, celiac disease and Crohn's disease.

13. The method according to claim 12, wherein the composition is administered in an amount sufficient to improve at least one of gastro-intestinal comfort and intestinal flora.

14. The method according to claim 12, wherein the composition is administered in an amount sufficient to treat the disease or disorder.

15. The method according to claim 9, wherein said yeast cells of at least one of said yeast strains are in a dry or fresh form.

16. The method according to claim 15, wherein said yeast cells of at least one of said yeast strains are in an instantaneous dry or active dry form.

17. The method according to claim 9, wherein said yeast cells of at least one of said yeast strains are administered at a daily dose comprised between $10^7$ and $6 \times 10^{10}$ CFU.

18. The method according to claim 17, wherein said yeast cells of at least one of said yeast strains are administered at a daily dose comprised between $10^8$ and $2 \times 10^{10}$ CFU.

19. The method according to claim 9, wherein the composition is administered at a daily dose comprised between 1 mg and 10 g.

20. The method according to claim 19, wherein the composition is administered at a daily dose comprised between 1 mg and 1 g.

21. A method treating a bowel pathology or disorder in a subject comprising a step of administering to said subject an effective amount of the composition according to claim 1.

22. The method according to claim 21, wherein the bowel disease or disorder is selected from functional intestinal disorders, functional intestinal pain syndrome, chronic inflammatory bowel diseases, food intolerances, irritable bowel syndrome, ulcerative colitis, hemorrhagic rectocolitis, celiac disease and Crohn's disease.

23. The method according to claim 21, wherein the composition is administered in an amount sufficient to improve at least one of gastro-intestinal comfort and intestinal flora.

24. The method according to claim 21, wherein said yeast cells of at least one of said yeast strains are in a dry or fresh form.

25. The method according to claim 24, wherein said yeast cells of at least one of said yeast strains are in an instantaneous dry or active dry form.

26. The method according to claim 21, wherein said yeast cells of at least one of said yeast strains are administered at a daily dose comprised between $10^7$ and $6 \times 10^{10}$ CFU.

27. The method according to claim 26, wherein said yeast cells of at least one of said yeast strains are administered at a daily dose comprised between $10^8$ and $2 \times 10^{10}$ CFU.

28. The method according to claim 21, wherein the composition is administered at a daily dose comprised between 1 mg and 10 g.

29. The method according to claim 28, wherein the composition is administered at a daily dose comprised between 1 mg and 1 g.

30. A kit of yeast cells comprising:
(i) cells having all of the identifying characteristics of *Saccharomyces cerevisiae* yeast the strain deposited at the Collection Nationale de Cultures de Microorganismes under No. CNCM I-3856, and/or
(ii) cells having all of the identifying characteristics of *Saccharomyces cerevisiae* var. *boulardii* yeast obtained from the strain deposited at the Collection Nationale de Cultures de Microorganismes under No. CNCM I-3799.
in a form suitable for oral administration.

* * * * *